(12) United States Patent
Fryshman

(10) Patent No.: US 10,328,249 B2
(45) Date of Patent: Jun. 25, 2019

(54) APPLICATIONS USING INDUCTION

(71) Applicant: Bernard Fryshman, Brooklyn, NY (US)

(72) Inventor: Bernard Fryshman, Brooklyn, NY (US)

(*) Notice: Subject to any disclaimer, the term of this patent is extended or adjusted under 35 U.S.C. 154(b) by 0 days.

(21) Appl. No.: 15/959,475

(22) Filed: Apr. 23, 2018

(65) Prior Publication Data

US 2018/0318569 A1  Nov. 8, 2018

Related U.S. Application Data

(60) Provisional application No. 62/500,380, filed on May 2, 2017, provisional application No. 62/507,894, filed on May 18, 2017.

(51) Int. Cl.
| | |
|---|---|
| *A23L 5/10* | (2016.01) |
| *A47J 36/02* | (2006.01) |
| *A61B 5/06* | (2006.01) |
| *A61K 41/00* | (2006.01) |
| *A61K 9/48* | (2006.01) |

(Continued)

(52) U.S. Cl.
CPC .............. *A61M 37/00* (2013.01); *A23L 5/15* (2016.08); *A47J 36/02* (2013.01); *A61B 5/065* (2013.01); *A61K 9/4816* (2013.01); *A61K 41/0028* (2013.01); *A61K 41/0052* (2013.01); *H05B 6/105* (2013.01); *H05B 6/12* (2013.01); *A23V 2002/00* (2013.01); *A61M 2205/18* (2013.01); *A61M 2205/368* (2013.01); *B01L 7/00* (2013.01); *B01L 2300/1816* (2013.01); *H01M 10/615* (2015.04); *H01M 10/625* (2015.04);

(Continued)

(58) Field of Classification Search
CPC ........ A61K 9/0097; A61M 2205/0244; A61M 2005/04; A61M 37/00; A61M 2205/368; A61M 2205/3686; A61N 1/0412; A61N 1/0428; A61N 1/0448
See application file for complete search history.

(56) References Cited

U.S. PATENT DOCUMENTS

| 3,138,698 A | 6/1964 | Wells et al. |
|---|---|---|
| 3,221,638 A | 12/1965 | Wickenberg |

(Continued)

FOREIGN PATENT DOCUMENTS

| CN | 205953976 | 2/2017 |
|---|---|---|
| JP | 07-275578 A | 10/1995 |

(Continued)

*Primary Examiner* — Bhisma Mehta
*Assistant Examiner* — William R Frehe
(74) *Attorney, Agent, or Firm* — Foley & Lardner LLP

(57) ABSTRACT

A system and method comprise positioning a medical device within a subject. The medical device includes a plurality of compartments and each of the plurality of compartments includes a ferrous material. Further, each of the plurality of compartments is configured to hold a substance. The system and method further include delivering electromagnetic radiation, by an electromagnetic radiation source, to the medical device and varying, by a controller, an amount of the electromagnetic radiation delivered by the electromagnetic radiation source for selectively heating the ferrous material of at least one of the plurality of compartments and selectively releasing the substance held in the at least one of the plurality of compartments for managing a condition.

18 Claims, 24 Drawing Sheets

(51) Int. Cl.
  *A61M 37/00* (2006.01)
  *H05B 6/12* (2006.01)
  *H05B 6/10* (2006.01)
  *H01M 10/657* (2014.01)
  *B01L 7/00* (2006.01)
  *H01M 10/625* (2014.01)
  *H01M 10/615* (2014.01)

(52) U.S. Cl.
  CPC ...... *H01M 10/657* (2015.04); *H01M 2220/20* (2013.01)

(56) References Cited

U.S. PATENT DOCUMENTS

| | | | |
|---|---|---|---|
| 3,494,722 A | | 2/1970 | Gray |
| 3,745,290 A | | 7/1973 | Harnden et al. |
| 3,790,735 A | | 2/1974 | Peters, Jr. |
| 4,020,310 A | | 4/1977 | Souder et al. |
| 4,418,259 A | | 11/1983 | Lewis |
| 4,766,879 A | | 8/1988 | Freese |
| 4,776,386 A | | 10/1988 | Meier |
| 4,830,855 A | * | 5/1989 | Stewart ............... A61K 9/2027 424/416 |
| 4,999,467 A | | 3/1991 | Iguchi |
| 5,053,593 A | | 10/1991 | Iguchi |
| 5,366,764 A | | 11/1994 | Sunthankar |
| 5,466,915 A | | 11/1995 | Meier et al. |
| 5,508,498 A | | 4/1996 | Rheinish et al. |
| 5,628,241 A | | 5/1997 | Chavanaz et al. |
| 5,665,258 A | | 9/1997 | Hsu |
| 5,665,263 A | | 9/1997 | Gaspard |
| 5,821,507 A | | 10/1998 | Sasaki et al. |
| 5,979,673 A | | 11/1999 | Dooley |
| 6,663,615 B1 | * | 12/2003 | Madou ............... A61K 9/0009 600/345 |
| 6,700,183 B2 | | 3/2004 | Jiang |
| 6,758,131 B1 | | 7/2004 | Joubert |
| 6,864,468 B2 | | 3/2005 | Kim et al. |
| 7,170,037 B2 | | 1/2007 | Walter |
| 8,803,045 B2 | | 8/2014 | Cadima |
| 9,820,690 B1 | | 11/2017 | Schwartz et al. |
| 2001/0035406 A1 | | 11/2001 | Ryan et al. |
| 2005/0065545 A1 | | 3/2005 | Wallace |
| 2006/0102871 A1 | * | 5/2006 | Wang ................... A61L 27/446 252/62.51 R |
| 2007/0000915 A1 | | 1/2007 | Cheng |
| 2007/0023486 A1 | | 2/2007 | Matsuura et al. |
| 2010/0000980 A1 | | 1/2010 | Popescu |
| 2010/0155391 A1 | | 6/2010 | Koschberg et al. |
| 2010/0170892 A1 | | 7/2010 | Wilson et al. |
| 2011/0245914 A1 | * | 10/2011 | Santini, Jr. ............... A23L 2/52 623/1.42 |
| 2011/0311455 A1 | * | 12/2011 | Anvari ..................... C12N 7/00 424/9.3 |
| 2012/0041286 A1 | * | 2/2012 | Goodall ................ A61L 2/0011 600/309 |
| 2013/0062527 A1 | * | 3/2013 | Hyde ................... A61N 5/1048 250/366 |
| 2013/0153565 A1 | | 6/2013 | Fryshman |
| 2014/0042170 A1 | | 2/2014 | Correa |
| 2014/0165607 A1 | | 6/2014 | Alexander |
| 2014/0217090 A1 | | 8/2014 | Fryshman |
| 2014/0238383 A1 | | 8/2014 | Armstrong |
| 2015/0126964 A1 | | 5/2015 | Martel et al. |
| 2016/0311542 A1 | | 10/2016 | Mackin |
| 2016/0370322 A1 | | 12/2016 | Hull et al. |
| 2018/0050218 A1 | * | 2/2018 | Copty ................... A61N 5/025 |

FOREIGN PATENT DOCUMENTS

JP          2006-172727 A      6/2006
WO          WO-2010/002751     1/2010

* cited by examiner

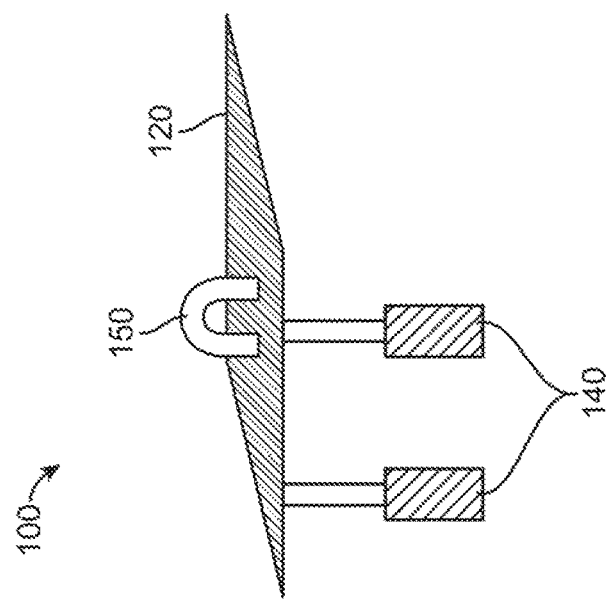
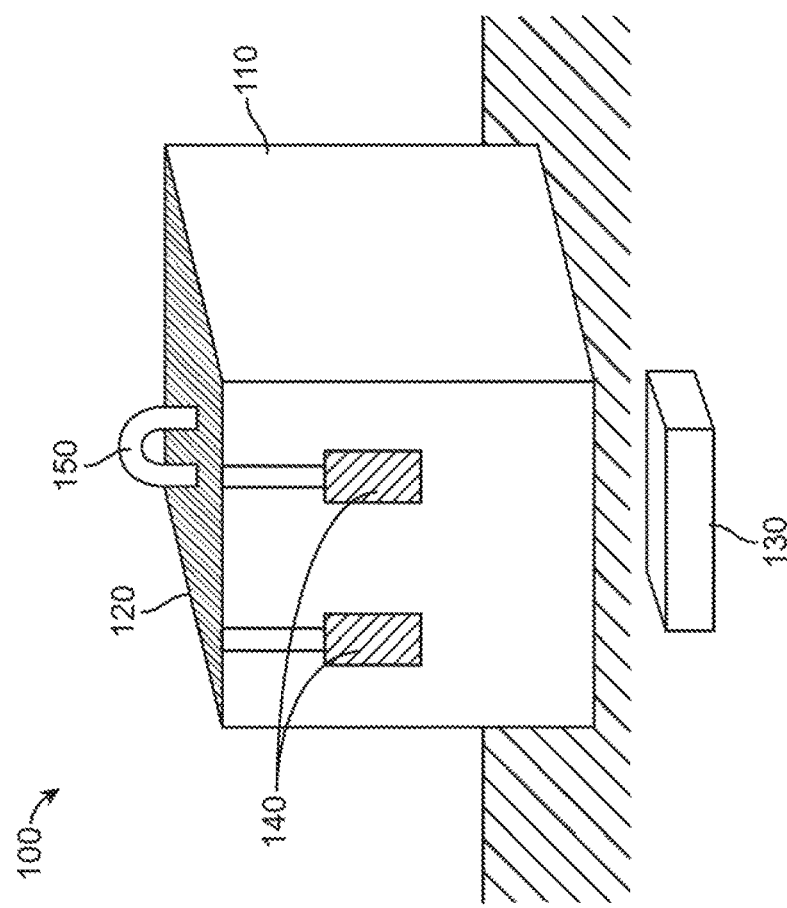

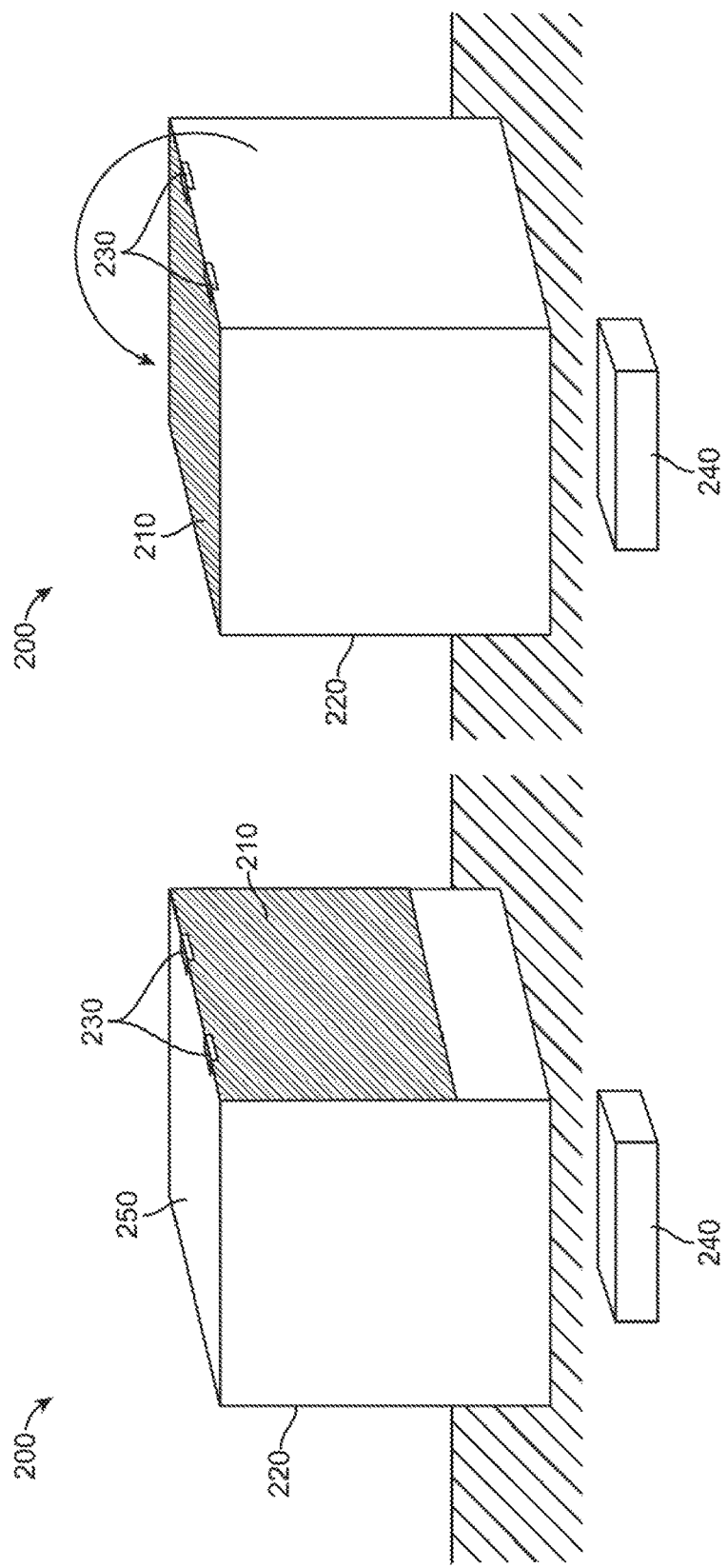

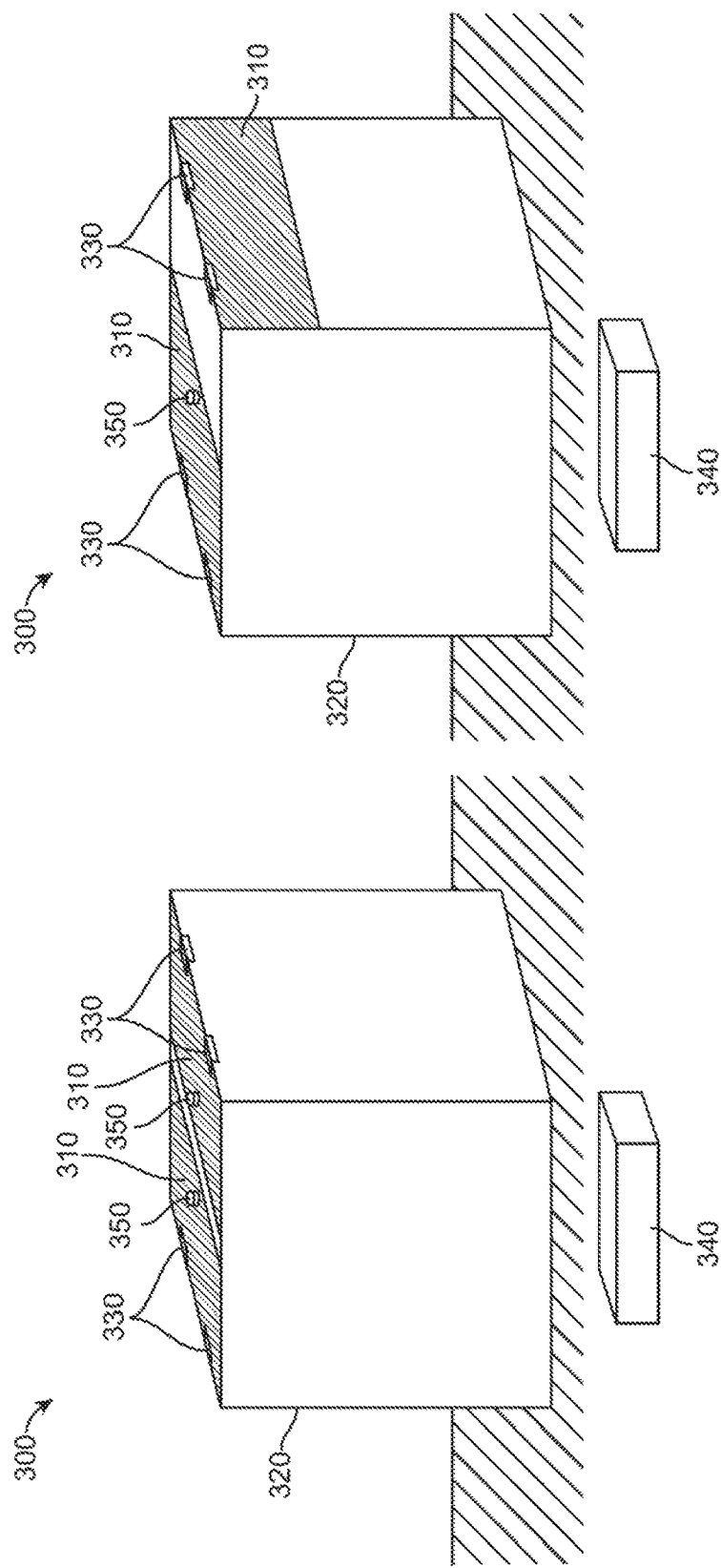

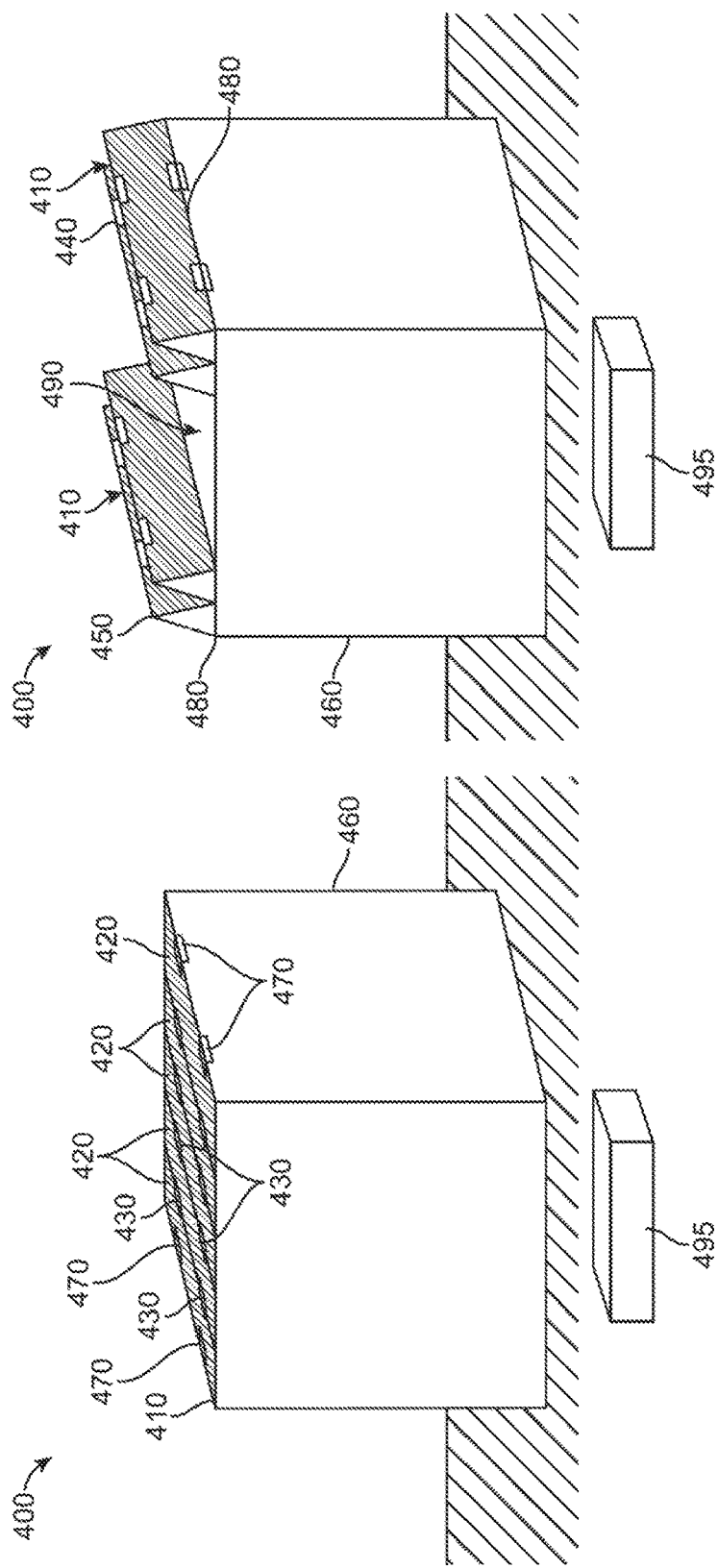

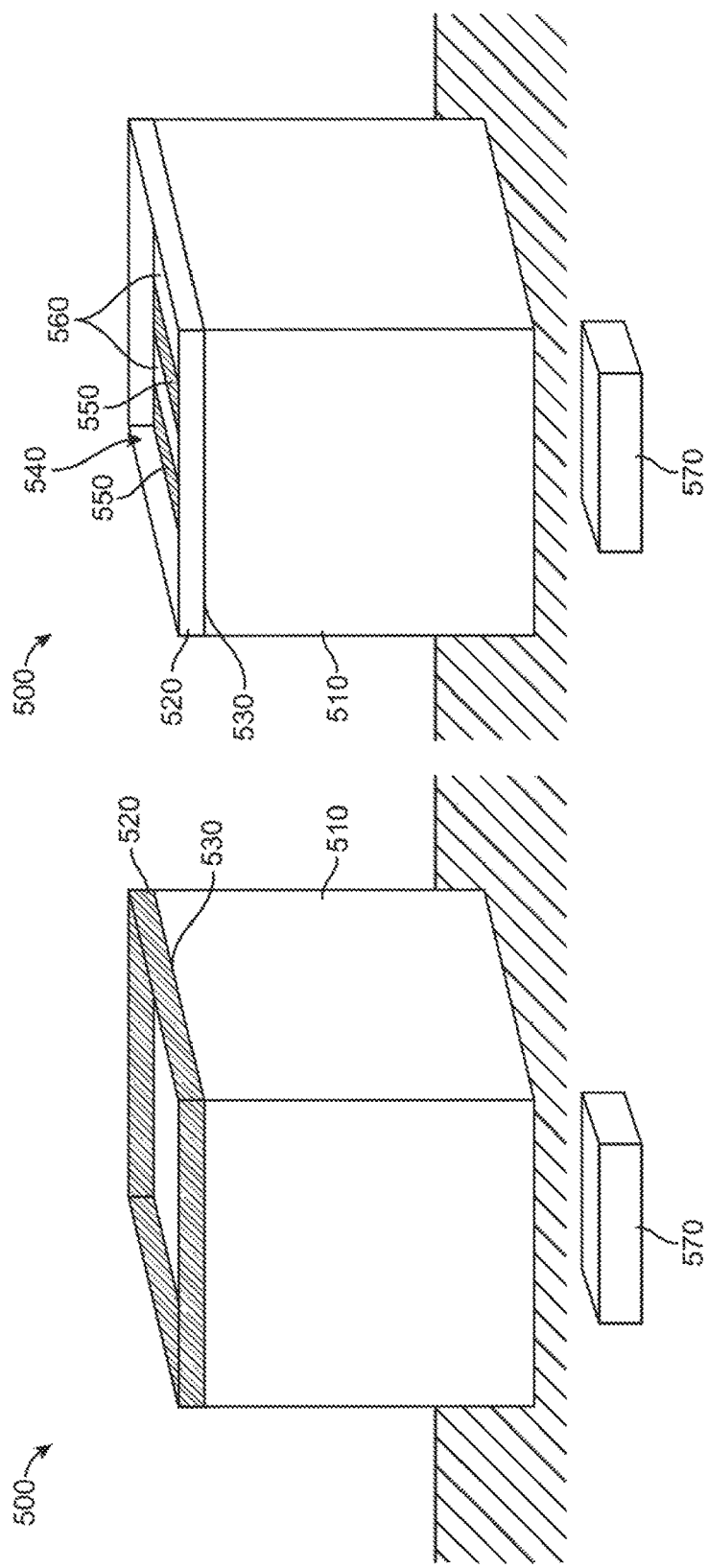

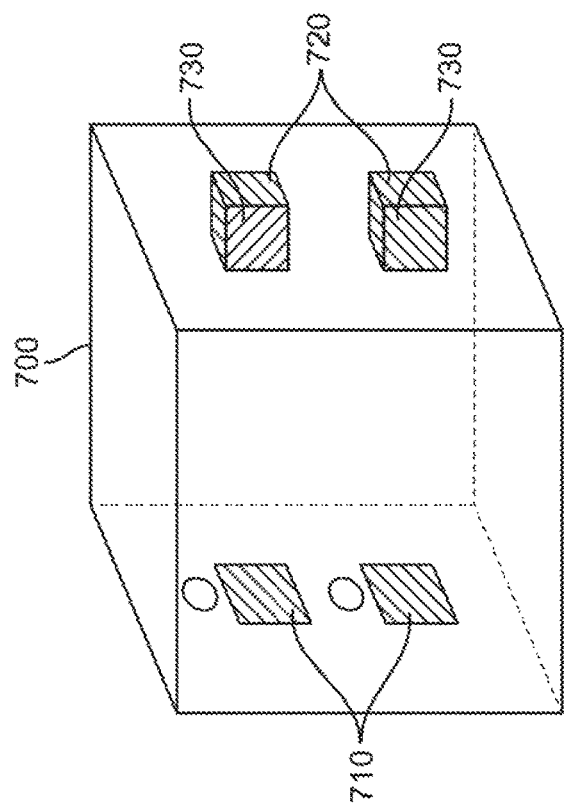
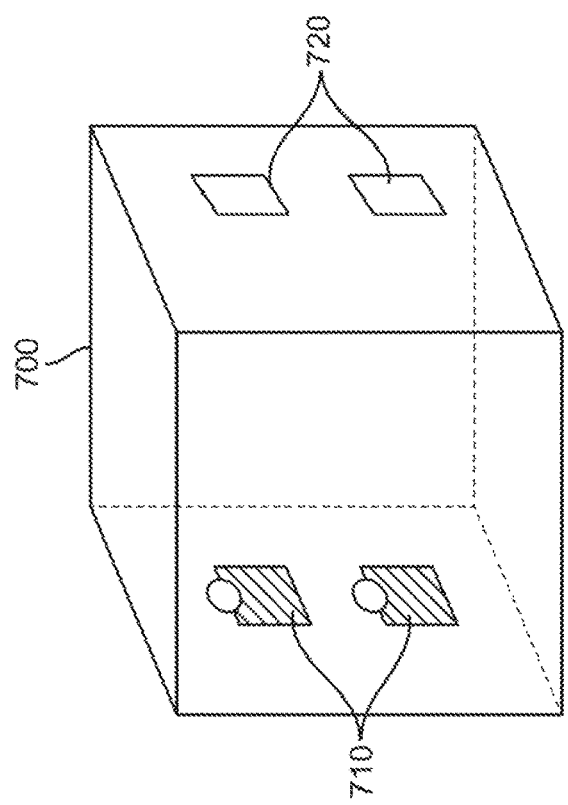
FIG. 7A
FIG. 7B

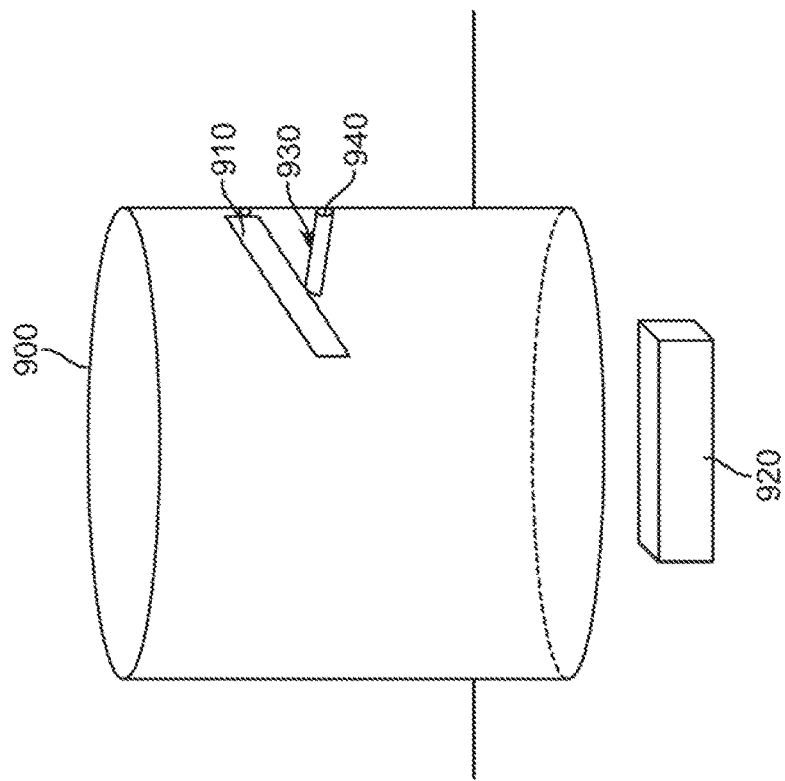
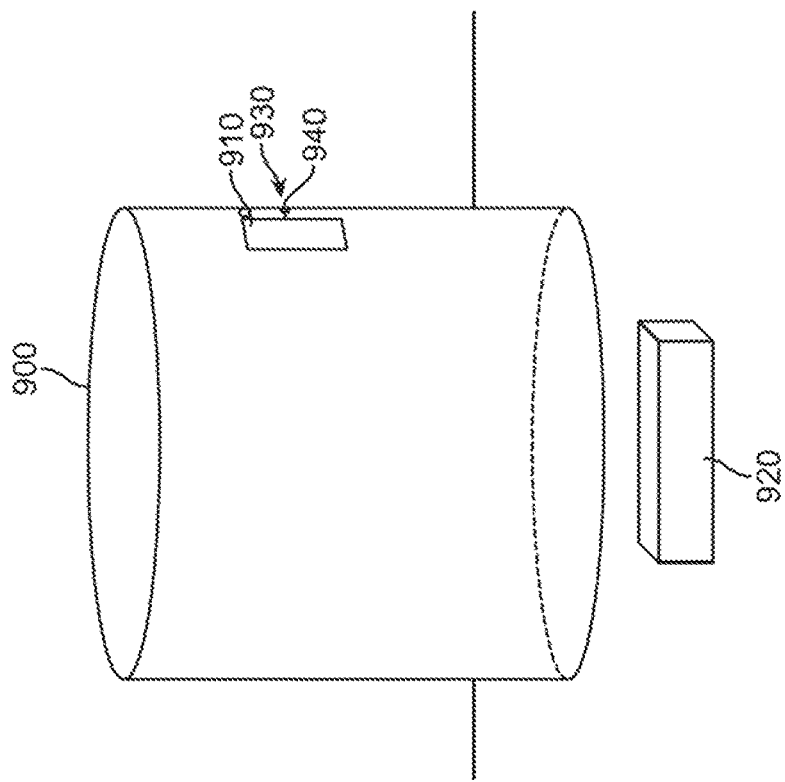

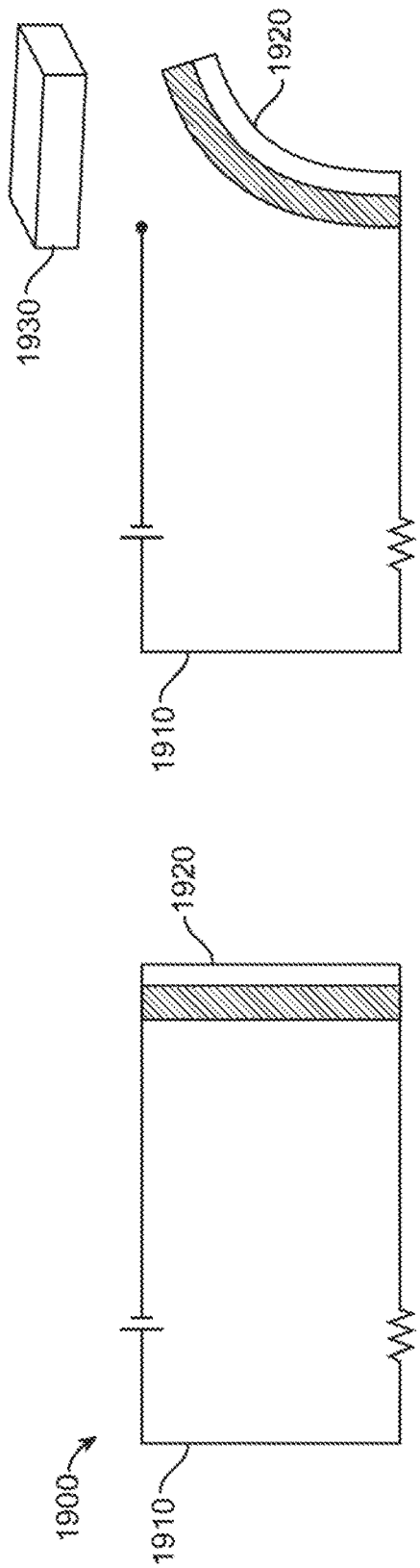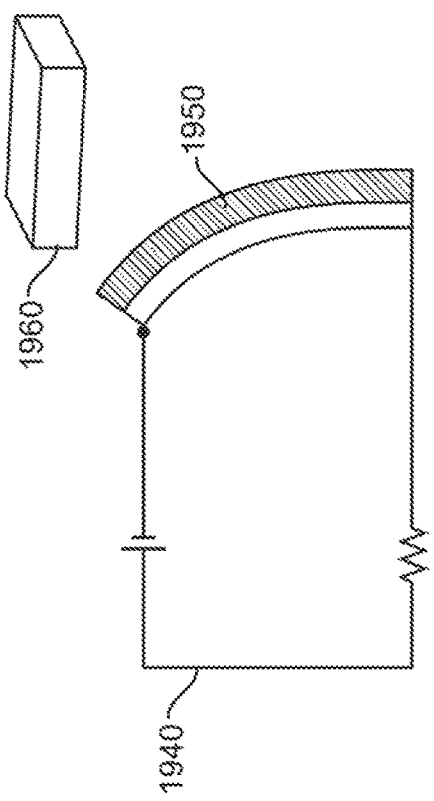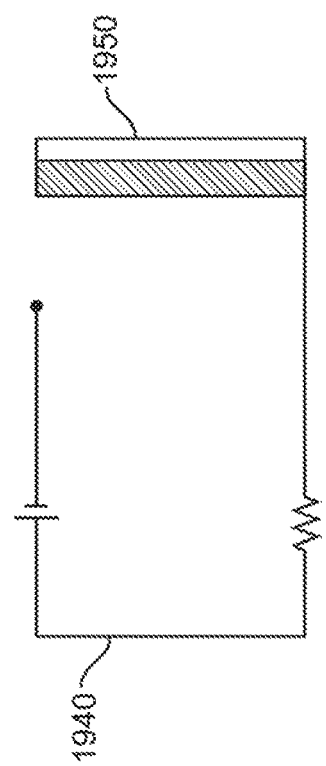

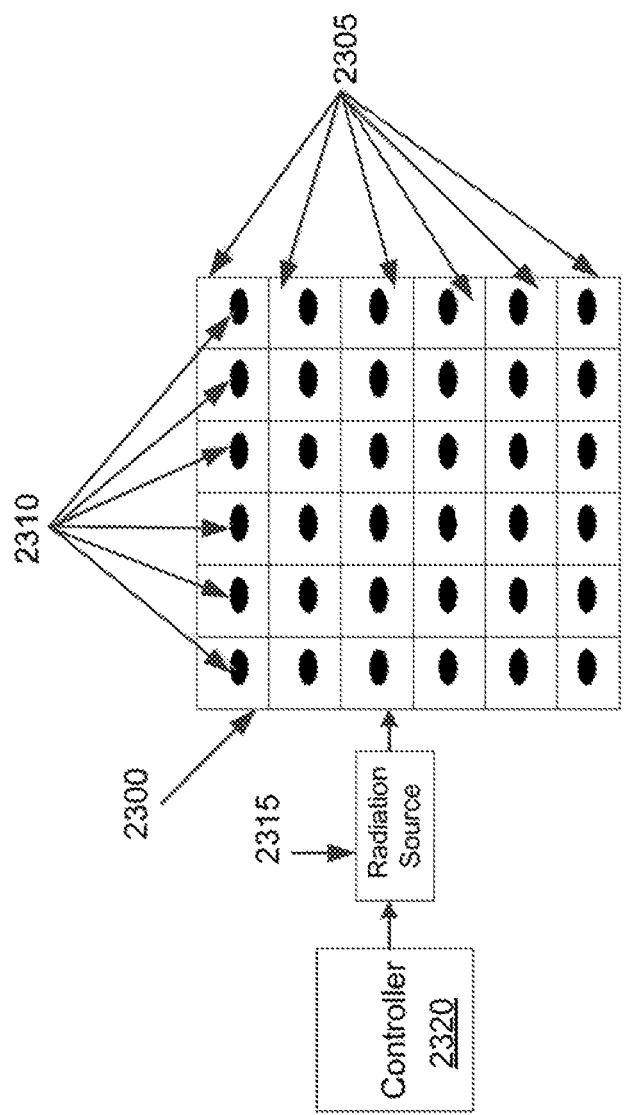

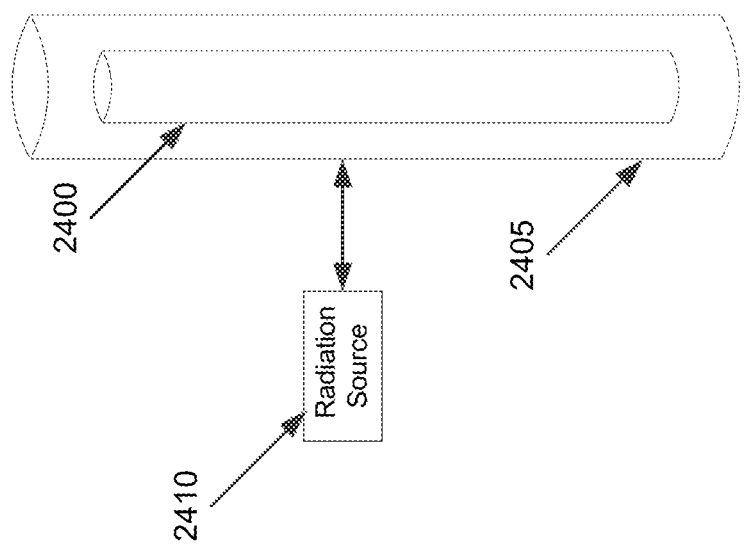

APPLICATIONS USING INDUCTION

CROSS-REFERENCE TO RELATED PATENT APPLICATIONS

The present application claims priority from U.S. Provisional Patent Application No. 62/500,380, filed on May 2, 2017, and U.S. Provisional Patent Application No. 62/507,894, filed on May 18, 2017, both of which are incorporated by reference in their entirety herein.

BACKGROUND

Induction cooking is a form of cooking that utilizes an electromagnetic radiation source, as opposed to thermal conduction from an open flame or electrical heating element, to heat a ferrous metal. Specifically, traditional induction cooking involves using a ferrous cooking vessel (e.g., a cooking vessel made up of a metal or alloy having iron therein) in conjunction with an electromagnetic radiation source. Upon activation, the electromagnetic radiation source emits electromagnetic waves or radiation that cause the ferrous cooking vessel to heat up, thereby heating the contents of the ferrous cooking vessel. As discussed throughout, the embodiments described herein represent a departure from traditional induction cooking and traditional uses of induction technology.

SUMMARY OF THE INVENTION

In accordance with some aspects of the present disclosure, a method is disclosed. The method includes positioning a medical device within a subject. The medical device includes a plurality of compartments and each of the plurality of compartments includes a ferrous material. Further, each of the plurality of compartments is configured to hold a substance. The method further includes delivering electromagnetic radiation, by an electromagnetic radiation source, to the medical device and varying, by a controller, an amount of the electromagnetic radiation delivered by the electromagnetic radiation source for selectively heating the ferrous material of at least one of the plurality of compartments and selectively releasing the substance held in the at least one of the plurality of compartments for managing a condition.

In accordance with some other aspects of the present disclosure, a system is disclosed. The system includes a medical device configured to be positioned within a subject. The medical device includes a plurality of compartments and each of the plurality of compartments is configured to hold a substance. Each of the plurality of compartments includes a ferrous material and each of the plurality of compartments is configured to selectively dispense the substance held within a respective one of the plurality of compartments upon heating the ferrous material of the respective one of the plurality of compartments.

In accordance with yet other aspects of the present disclosure, a system is disclosed. The system includes a sleeve having a ferrous material. The sleeve is configured to encompass at least a portion of an object. The system also includes an electromagnetic radiation source associated with the sleeve and configured to deliver electromagnetic radiation to heat the ferrous material of the sleeve such that the heat from the ferrous material is transferred to the object for heating the object.

The foregoing is a summary of the disclosure and thus by necessity contains simplifications, generalizations, and omissions of detail. Consequently, those skilled in the art will appreciate that the summary is illustrative only and is not intended to be in any way limiting. Other aspects, features, and advantages of the devices and/or processes described herein, as defined by the claims, will become apparent in the detailed description set forth herein and taken in conjunction with the accompanying drawings.

BRIEF DESCRIPTION OF THE DRAWINGS

FIGS. 1A and 1B depict an induction based cooking system having a non-ferrous cooking vessel with a cover of material subject to heating by induction (i.e., induction cooking cover), in accordance with at least some embodiments of the present disclosure.

FIGS. 2A and 2B depict an induction based cooking system having a non-ferrous cooking vessel with a hinged induction cooking cover, in accordance with at least some embodiments of the present disclosure.

FIGS. 3A and 3B depict an induction based cooking system having a non-ferrous cooking vessel with a hinged induction two-piece cooking cover, in accordance with at least some embodiments of the present disclosure.

FIGS. 4A and 4B depict an induction based cooking system having a non-ferrous cooking vessel with an accordion style induction cooking cover, in accordance with at least some embodiments of the present disclosure.

FIGS. 5A and 5B depict an induction based cooking system having a non-ferrous cooking vessel with a frame that is configured to receive one or more ferrous cover elements, in accordance with at least some embodiments of the present disclosure.

FIGS. 7A and 7B depict a non-ferrous cooking vessel having slots therein to receive pieces of metal subject to heating by induction, inserted or removed from the non-ferrous cooking vessel to enable heating to take place in a targeted and controlled manner (i.e., induction heating elements), in accordance with at least some embodiments of the present disclosure.

FIGS. 9A and 9B depict a non-ferrous cooking vessel configured to receive a mobile induction heating element, in accordance with at least some embodiments of the present disclosure.

FIGS. 19A-19D depict circuit switches that are triggered by induction heating, in accordance with at least some embodiments of the present disclosure.

FIG. 23 depicts a medical device configured to facilitate controlled release of one or more medicines within a subject via induction heating, in accordance with at least some embodiments of the present disclosure.

FIG. 24 depicts an object protected using a ferromagnetic sleeve, in accordance with at least some embodiments of the present disclosure.

Figure 6:
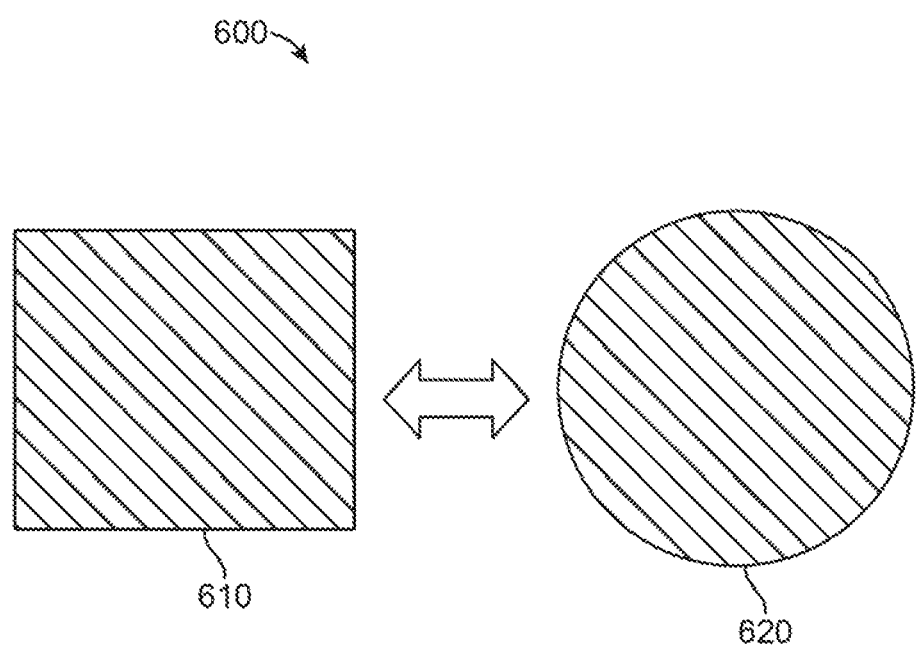
FIG. 6 depicts a transformable induction cooking cover, in accordance with at least some embodiments of the present disclosure.

It is noted that the above-referenced figures are representational, and that they are not intended to be limiting with respect to the form and/or shape of the various embodiments.

DETAILED DESCRIPTION

The present disclosure relates to applications of induction heating. For example, the present disclosure relates to induction cooking. Conventional induction cooking involves use of a cooking vessel made of a ferrous or similar material, where the cooking vessel receives electromagnetic energy from an electromagnetic radiation source. The electromagnetic energy from the electromagnetic radiation source heats the ferrous cooking vessel, which in turn causes the contents of the cooking vessel to cook. The present disclosure allows for induction cooking to take place in a cooking vessel that is made of a non-ferrous material. Specifically, to facilitate induction cooking using a non-ferrous cooking vessel, ferrous elements may be positioned on, around, or under the non-ferrous cooking vessel, incorporated into walls of the non-ferrous cooking vessel, form the lid/cover of the non-ferrous cooking vessel, used in conjunction with the non-ferrous cooking vessel etc. to facilitate the induction heating of the contents of the non-ferrous cooking vessel. In such implementations, the electromagnetic radiation from the electromagnetic radiation source travels to the ferrous elements of the non-ferrous cooking vessel to heat food in a strategic and targeted manner, as described in greater detail below.

Referring now to FIGS. 1A and 1B, an exemplary induction cooking system 100 is shown, in accordance with at least some embodiments of the present disclosure. Specifically referring to FIG. 1A, the induction cooking system 100 includes a cooking vessel 110 having a cooking cover 120. It is to be understood that the shape and size of the cooking vessel 110 and the cooking cover 120, as shown in FIGS. 1A and 1B, are merely exemplary. In other embodiments, the cooking vessel 110 and the cooking cover 120 may assume other shapes and sizes, as desired. Specifically, the cooking cover 120 may assume a variety of shapes and sizes corresponding to the shape and size of the cooking vessel 110. Furthermore, in at least some embodiments, at least a portion of the cooking cover 120 is made of a ferrous material and the cooking vessel 110 is made of a non-ferrous material.

Contents within the cooking vessel 110 are heated using a radiation source 130. In an illustrative embodiment, the radiation source 130 is a source of electromagnetic radiation. Furthermore, the distance between the radiation source 130 and the ferrous materials (e.g., the cooking cover 120) may be varied but kept within a commonly known range to effectively facilitate heating of the ferrous materials. Likewise, the positioning (e.g., orientation and angle) of the radiation source 130 relative to the ferrous materials (e.g., the cooking cover 120) may be varied to achieve a desired heating profile. As used herein, "heating profile" means the direction, angle, and intensity of heat that is desired to effectively and appropriately heat the contents of the cooking vessel 110.

Thus, electromagnetic radiation from the radiation source 130 is used to heat the ferrous portions of the induction cooking system 100, such as the cooking cover 120. The cooking cover 120 then transfers the heat to the contents of the cooking vessel 110 to heat the contents therein. Since the cooking vessel 110 is made of a non-ferrous material, the radiation source 130 does not heat the cooking vessel 110. The radiation source 130 only heats the cooking cover 120, which is ferrous in nature. By virtue of heating the contents of the cooking vessel 110 using the cooking cover 120, the contents (e.g., food) of the cooking vessel are strategically heated from the top, as opposed to the bottom.

Furthermore, in at least some embodiments and, as shown in FIGS. 1A and 1B, the cooking cover 120 includes induction heating elements 140 suspended from the cooking cover. The cooking cover can be ferrous or at least partially ferrous in an illustrative embodiment. Alternatively, the cooking cover may be non-ferrous. FIGS. 1A and 1B illustrate two of the induction heating elements 140. In alternative embodiments, additional or fewer than two of the induction heating elements 140 may be used. For example, in some embodiments, a single induction heating element may be used, while in other embodiments, three, four, five, or possibly greater number of induction heating elements may be used. Furthermore, the shape, size, and configuration of the induction heating elements 140 may vary from one embodiment to another.

Additionally, for a given one of the cooking cover 120, the shape, size, and configuration of each of the induction heating elements 140 may vary from another one of the induction heating element. Likewise, the placement of each of the induction heating elements 140 may vary on the cooking cover 120. For example, in at least some embodiments, each of the induction heating elements 140 may be positioned equidistant from one another—whether closer to the center of the cooking cover 120 or closer to the periphery of the cooking cover. In other embodiments, the induction heating elements 140 need not be positioned equidistant from one another. Rather, the positioning of the induction heating elements 140 may vary depending upon the heating profile of the contents within the cooking vessel 110 that is desired.

Furthermore, in some embodiments and as shown, the induction heating elements 140 may be hung from the bottom of the cooking cover 120. Each of the induction heating elements 140 may be hung using a hook/loop attachment, magnetic attachment, other attachment mechanism, or integrally formed as a unitary piece of the cooking cover 120. By virtue of extending downwardly from the bottom of the cooking cover 120, the induction heating elements 140 extend into the cooking vessel 110 and, thus, may be positioned relative to the food/contents of the cooking vessel to strategically heat the contents of the cooking vessel. Additionally, in some embodiments, the induction heating elements 140 may be extendable/retractable such that they may be lowered into or raised above the contents of the cooking vessel 110, as desired. Such an extendable/retractable feature may be implemented using a telescoping induction heating element, by a segmented induction heating element in which portions can be added and removed, and/or by a hinged induction heating element in which hinged portions of the induction heating element can be raised or lowered.

While the induction heating elements 140 have been shown and described as extending downwardly from the cooking cover 120, in other embodiments, the induction heating elements may be provided to extend into the cooking vessel 110 from the sides of the cooking vessel or from the bottom of the cooking vessel. These additional ones of the induction heating elements 140 (e.g., the induction heating elements extending from the sides or bottom of the cooking vessel) may be provided in addition to or instead of the induction heating elements extending downwardly from the cooking cover 120.

In at least some embodiments, the cooking cover 120 also includes a handle 150. In at least some embodiments, the handle 150 is made from a heat resistant, non-ferrous material (e.g., wood, glass, ceramic, etc.) such that it is not directly heated as a result of the electromagnetic radiation that heats the rest of the cooking cover 120. The size, shape, configuration, placement, etc. of the handle 150 may vary in different embodiments, and is not limited to the example configuration illustrated in FIGS. 1A and 1B. In at least some embodiments, more than a single one of the handle 150 may be provided as well.

While the induction cooking system 100 described above has been described as having the cooking vessel 110 that is made of a non-ferrous material and the cooking cover 120 that is made of a ferrous material, it is to be understood that in at least some embodiments, variations are contemplated. For example, in some embodiments, only portions of the cooking vessel 110 may be made of a non-ferrous material such that the cooking vessel 110 may be partly made of a ferrous material. Likewise, in some embodiments, only portions of the cooking cover 120 may be made of a ferrous material with the remaining portions of the cooking cover made of a non-ferrous material.

In general, the portions of the cooking vessel 110 and the cooking cover 120 that are ferrous and non-ferrous depend upon the heating profile of the contents of the vessel that is desired. Additionally, while the induction cooking system 100 has been described from the perspective of cooking food, it is to be understood that the present disclosure (including the embodiments described below) may be used in applications other than cooking. For example, the induction cooking system 100 may be used in any application that requires heating of any contents (food or non-food) within the cooking vessel 110 by using induction heat.

Turning now to FIGS. 2A and 2B, an induction cooking system 200 is shown, in accordance with at least some embodiments of the present disclosure. The induction cooking system 200 includes a cooking cover 210 attached to a cooking vessel 220 via hinges 230. While the embodiments of FIGS. 2A and 2B show the cooking cover 210 as attached to the cooking vessel 220 via two of the hinges 230, in other embodiments, additional or fewer hinges may be used. Additionally, a connection mechanism other than the hinges 230 may be used in other embodiments to movably attach the cooking cover 210 to the cooking vessel 220. Furthermore, the hinges 230 may be made of a ferrous or a non-ferrous material. Again, and similar to the cooking vessel 110 and the cooking cover 120, the shape and size of the cooking cover 210 and the cooking vessel 220 may vary from one embodiment to another.

In at least some embodiments, the cooking cover 210 is made of a ferrous material and the cooking vessel 220 is made from a non-ferrous material. Thus, the cooking cover 220 generates heat upon receipt of electromagnetic energy from a radiation source 240. Similar to the radiation source 130, the radiation source 240 is a source capable of generating electromagnetic radiation for heating ferrous materials. Also similar to the radiation source 130, the positioning and orientation of the radiation source 240 may vary from one embodiment to another. Furthermore, as is known to those of skill in the art, the orientation of the ferrous material relative to the electromagnetic radiation affects the intensity of heat generated by the ferrous material (in this case the cooking cover 210). Thus, by virtue of varying the orientation of the cooking cover 210 relative to the radiation source 240, the heat generated by the cooking cover may be varied to vary the heat delivered to the contents of the cooking vessel 220.

Specifically, in FIG. 2A, the cooking cover 210 is shown in an open position, such that an opening 250 is present on the top of the cooking vessel 220 revealing any contents of the cooking vessel. In this open position, the cooking cover 210 is oriented parallel to the electromagnetic radiation emitted from the radiation source 240. On the other hand, FIG. 2B depicts the cooking cover 210 in a closed position such that any contents of the cooking vessel 220 are not visible from the opening 250. In this closed position, the cooking cover 210 is oriented perpendicular to the electromagnetic radiation emitted from the radiation source 240. Thus, the heat profile generated by the cooking cover 210 in an open position is different from the heat profile generated by the cooking cover in a closed position. In other embodiments, the hinges 230 may allow for more than a parallel and perpendicular orientation of the cooking cover 210 relative to the radiation source 240, such that the intensity of heat may be varied as desired by the user. For example, the hinges 230 (or any other attachment mechanism that is used) may include a sufficient amount of friction to hold the cooking cover 210 in any desired position between the fully open position (FIG. 2A) and the fully closed position (FIG. 2B). The variation of heat intensity may alternatively or in addition to the movement of the cooking cover 210 be achieved by varying the position and/or orientation of the radiation source 240.

Furthermore, while not shown in FIGS. 2A and 2B, the cooking cover 210 may also include a handle similar to the handle 150 of FIGS. 1A and 1B. Additionally, the cooking cover 210 and/or the cooking vessel 220 may include induction heating elements similar to the induction heating elements 140. Moreover, portions of the cooking cover 210 may be made of a non-ferrous material and/or portions of the cooking vessel 220 may be made of a ferrous material in some embodiments. Also, the hinges 230 or other flexible connectors used to connect the cooking cover 210 to the cooking vessel 220 may be used in other embodiments to implement a variety of cooking covers and associated cooking vessels, each of which may be associated with a desired cooking strategy. Some of the variations of flexible connectors/hinges are shown in FIGS. 3A/3B and 4A/4B below.

Referring specifically to FIGS. 3A and 3B, an induction cooking system 300 having a cooking cover 310 is shown, in accordance with at least some embodiments of the present disclosure. Specifically, in at least some embodiments, the cooking cover 310 is a hinged two-piece cooking cover. The cooking cover 310, which is made at least partially from a ferrous material, is attached to a cooking vessel 320 via hinges 330 on two sides of the cooking vessel. The cooking vessel 320 may be at least partially non-ferrous. While two of the hinges 330 are shown to connect each side of the cooking vessel 320 to the cooking cover 310, it is to be understood that additional or fewer hinges may be used on each side. It is also to be understood that attachment mechanisms other than the hinges 330 may be used to connect the cooking cover 310 to the cooking vessel 320.

Furthermore, each piece of the cooking cover 310 may be individually manipulated to achieve various configurations and orientations relative to both the contents of the cooking vessel 320 and a radiation source 340. As discussed above, the angle of the ferrous material relative to the electromagnetic radiation from the radiation source 340 may be varied to vary the intensity of heat delivered to the cooking vessel 320. As such, a user may control the heat delivered to the contents of the cooking vessel 320 to a desired level by varying the angular positioning of one or both of the radiation source 340 and each piece of the cooking cover 310.

FIG. 3A depicts both pieces of the cooking cover 310 in a closed position (i.e., covering the top opening of the cooking vessel 320). FIG. 3B depicts one piece of the cooking cover 310 in a closed position and the other piece in an open position such that the top opening of the cooking vessel 320 is partially open and partially closed and attains a heat profile that is at least somewhat different from the heat profile of the configuration of FIG. 3A. Similar to the cooking cover 210, in at least some embodiments, each piece of the cooking cover 310 is connected to the cooking vessel 320 via the hinges 330 (or other attachment mechanism) to achieve a plurality of angular positions between the fully open position and the fully closed position to adjust the heat profile.

In at least some embodiments, each piece of the cooking cover 310 also includes a handle 350 that may be made of a non-ferrous material to facilitate opening and closing of the respective piece of the cooking cover. Each of the two pieces of the cooking cover 310 may also be detachable/removable from the cooking vessel 320 in some embodiments. Furthermore, the two pieces of the cooking cover 310 need not be of equal size. Rather, in some embodiments, one piece of the cooking cover 310 may be of a larger size than the other piece to further manipulate the heating profile. In another embodiment, the cooking cover 310 may include a plurality of handles for stylistic effect and/or for hanging the cooking cover 310. The handle(s) can be folded such that cooking vessels can be stacked upon one another with the cooking covers in place. The cooking cover may also be removable for storing, washing, and/or for use as a serving dish.

Also, in at least some embodiments, the cooking cover 310 and/or the cooking vessel 320 may have induction heating elements (e.g., similar to the induction heating elements 140 of FIGS. 1A and 1B) to further adjust the heat generated by the ferrous portions of the induction cooking system 300. Furthermore, while the embodiment above has been described as each piece of the cooking cover 310 being made of a ferrous material, in at least some embodiments, only portions of one or both pieces of the cooking cover may be made of a ferrous material with the remaining portions being made of a non-ferrous material. Specifically, the combination of the ferrous and non-ferrous materials in one or both pieces of the cooking cover 310 depends upon the heating profile that is desired. Also and as mentioned above, the cooking cover 310 may be attached to the cooking vessel 320 by movable mechanisms other than hinges.

Turning now to FIGS. 4A and 4B, an induction cooking system 400 is shown, in accordance with at least some embodiments of the present disclosure. The induction cooking system 400 includes an accordion style cooking cover 410 having a plurality of sections 420 that are connected to one another via hinges 430 or another attachment mechanism that allows the plurality of sections to fold in a manner described below. Specifically and as shown in FIG. 4B, the accordion style cooking cover 410 includes two jointed portions 440 and 450. Each of the two jointed portions 440 and 450 are attached to one side of a cooking vessel 460 (e.g., in a manner similar to the cooking cover 310 of FIGS. 3A and 3B). In at least some embodiments, hinges 470 may be used to movably attach each of the two jointed portions 440 and 450 to the cooking vessel 460. In other embodiments, other mechanisms may be used to connect the two jointed portions 440 and 450 of the accordion style cooking cover 410 to the cooking vessel 460.

Furthermore, each of the two jointed portions 440 and 450 may be rolled/folded toward an outside edge 480 (see FIG. 4B) of the cooking vessel 460 to provide an opening 490 (see FIG. 4B) at the top of the cooking vessel. FIG. 4A depicts the accordion style cooking cover 410 in a closed position and FIG. 4B depicts the accordion style cooking cover in a substantially open position. The opening 490 of the cooking vessel 460 may be varied by folding or unfolding the jointed portions 440 and 450 until the opening is of a desired size. By virtue of varying the opening 490 of the cooking vessel 460, a user may adjust the position of the accordion style cooking cover 410 based on desired heat and cooking preferences (in a manner described above in FIGS. 2A/2B and 3A/3B).

While the accordion style cooking cover 410 has been described above as having the two jointed portions 440 and 450 and each of the jointed portions having a plurality of sections 420, other variations of the accordion style cooking cover are contemplated and considered within the scope of this present disclosure. For example, in an alternative embodiment, the accordion style cooking cover 410 may be a single hinged cover that gets rolled/folded towards a single edge/side of the cooking vessel 460. In other embodiments, the accordion style cooking cover 410 may be made of more than two of the jointed portions 440 and 450 and each of the jointed portions may include a plurality of sections (such as the plurality of sections 420) connected flexibly with respect to one another. Additionally, in some embodiments, the accordion style cooking cover 410 may not be attached to the cooking vessel 460 at all and may, rather, simply rest on top of the cooking vessel. Other variations/configurations of the accordion style cooking cover 410 are also envisioned, and the description is not intended to be limited by the specific configuration of FIGS. 4A and 4B.

Furthermore, in at least some embodiments and as shown, each of the plurality of sections 420 of the accordion style cooking cover 410 are made of a ferrous material. In other embodiments, less than all of the plurality of sections 420 may be made of a ferrous material with the remaining ones of the plurality of sections being made of a non-ferrous material. Likewise, in at least some embodiments, at least a portion of the cooking vessel 460 may be made from a non-ferrous material. Again, the combination of the ferrous and non-ferrous material in the plurality of sections 420, as well as in the cooking vessel 460 depends upon the heating profile that is desired. By virtue of making at least some of the plurality of sections 420 of the accordion style cooking cover 410 of a ferrous material, the accordion style cooking cover may be heated by an electromagnetic radiation source 495, in a manner described above.

Moreover, while not shown, the induction cooking system 400 may be provided with one or more handles (e.g., similar to the handle 150 of FIGS. 1A/1B) and one or more induction heating elements (e.g., similar to the induction heating elements 140 of FIGS. 1A/1B).

Turning now to FIGS. 5A and 5B, yet another embodiment of an induction cooking system 500 is shown, in accordance with at least some embodiments of the present disclosure. The induction cooking system 500 includes a cooking vessel 510 and a frame 520 attached to or resting on a top perimeter 530 of the cooking vessel. The frame 520 is configured to receive one or more cover elements 540, in accordance with at least some embodiments. The frame 520 itself may be made of a ferrous or non-ferrous material, depending up on the implementation and the heating profile desired. For example, FIG. 5A shows the frame 520 as being made of a ferrous material, while FIG. 5B shows the frame as being made of a non-ferrous material.

Furthermore, in at least some embodiments, the frame 520 may be designed to be detachable from the cooking vessel 510, or in some embodiments, the frame may be permanently mounted on the cooking vessel. Additionally, in at least some embodiments, the cooking vessel 510 may be made of a non-ferrous material, while in other embodiments, a portion of the cooking vessel may be made of a ferrous material. Again, the ferrous/non-ferrous material combination of the cooking vessel 510 and the frame 520 depends upon the heating profile that is desired. Furthermore, the size of the frame 520 may vary from one embodiment to another depending upon the size of the cover elements 540 that the frame may receive and support.

In at least some embodiments, the cover elements 540 may include a combination of ferrous elements 550 that are made of a ferrous material and non-ferrous elements 560 that are made of a non-ferrous material. In other embodiments, all of the cover elements 540 may be made of a ferrous material. Further, while FIG. 5B shows the cover elements 540 as having two of the ferrous elements 550 and two of the non-ferrous elements 560, this is merely exemplary. The number of the ferrous elements 550 and the non-ferrous elements 560 may vary depending upon the heating profile that is desired. Additionally, in at least some embodiments, instead of using the non-ferrous elements 560, portions of the cooking vessel 510 may be left uncovered such that gaps may exist between the ferrous elements 550. Alternatively, in some embodiments, a combination of the ferrous elements 550, the non-ferrous elements 560, and uncovered spaces may be used.

Furthermore, a user may arrange the ferrous elements 550, the non-ferrous elements 560, and the open spaces to achieve a desired heating profile. Also, the number of the cover elements 540, their shape, their placement/orientation are all variable subject to the desired cooking style and needs of the user. Moreover, in at least some embodiments, the cover elements 540 may be detachably connected in any of a variety of ways to the frame 520, while in other embodiments, the cover elements may be permanently attached or built-in to the frame. The cover elements 540 and particularly the ferrous elements 550 of the cover elements receive electromagnetic radiation from a radiation source 570. The radiation source 570 is similar to the radiation source 130, 240, 340, and 495.

Additionally, as discussed above, the induction cooking system 500 may include one of more handles and/or one or more induction heating elements, as described above in FIGS. 1A and 1B, to achieve desired heating profiles.

Referring now to FIG. 6, a cooking cover 600 is shown, in accordance with at least some embodiments of the present disclosure. Specifically, the cooking cover 600 is a transformable cooking cover. In at least some embodiments, the cooking cover 600 is made from a ferrous material. In other embodiments, at least a portion of the cooking cover 600 may be made from a non-ferrous material. In a first configuration and as shown, the cooking cover 600 is a square cooking cover 610, and in a second configuration, the square cooking cover is transformed into a circular cooking cover 620. Notwithstanding the transformation of the cooking cover 600 from the square cooking cover 610 to the circular cooking cover 620, various other shapes and configurations of the cooking cover, both before and after the transformation are contemplated and considered within the scope of the present disclosure.

The transformation of the cooking cover 600 from one configuration to another may be accomplished in a variety of ways. For example and in one embodiment, the cooking cover 600 includes a plurality of hinged portions (not shown) that allow the cooking cover to be configured into a plurality of distinct shapes by varying the shape and size of the hinged portions (e.g., by folding/unfolding the hinged portions similar to the accordion style cooking cover 410, discussed above). Thus, to transform the square cooking cover 610 into the circular cooking cover 620, a hinged corner portion of each of the corners of the square cooking cover may be folded inward onto/over a remainder of the cooking cover such that circular portions of the circular cooking cover 620 are obtained. The circular cooking cover 620 may be transformed back into the square cooking cover 610 by unfolding the previously folded hinged portions.

Another mechanism of transforming the cooking cover 600 from one configuration to another may include sliding cover sections (also not shown). In such embodiments, the cooking cover 600 includes a plurality of cover sections capable of sliding over or under neighboring cover sections. As such, the cover sections may be layered until the desired shape/configuration of the cooking cover 600 is attained. For example, to transform the square cooking cover 610 into the circular cooking cover 620, the corner sections of the square cooking cover 610 may be slid under or over neighboring cover sections until the cooking cover achieves a circular shape of the circular cooking cover 620.

In some embodiments, the cooking cover 600 itself may be made of a plurality of layered sections such that the square cooking cover 610 may be transformed into the circular cooking cover 620 by sliding cover sections in between an upper and a lower layer of the cooking cover to form the circular cooking cover. In yet other embodiments, the cooking cover 600 may include a frame (e.g., similar to the frame 520). The frame may be made out of various flexible frame portions that may be molded (e.g., by varying the frame portions relative to one another) into various shapes. The frame may be designed to receive various ferrous and non-ferrous cover elements (e.g., similar to the cover elements 540). The cover elements may themselves be made of flexible portions that may change shape to adapt to the shape of the frame or a variety of sizes of the cover elements may be provided to accommodate the various shapes that the frame may be molded into. Other such mechanisms of varying the shape of the cooking cover 600 are contemplated.

By virtue of using transformable cooking covers (e.g., the cooking cover 600), the present disclosure allows a user to convert existing non-ferrous cooking vessels of varying shapes into induction cooking systems at a minimal cost. In addition, by targeting electromagnetic radiation on top of the cooking vessel and cover, such transformable cooking covers can be used to convert an existing ferrous cooking vessel into an induction cooking system.

Again, it is to be understood that while the explanation above has been with respect to the square cooking cover 610 transforming into the circular cooking cover 620, in alternative embodiments, the cooking cover 600 may be configured from and into additional shapes, such as rectangular, triangular, hexagonal, etc.

Thus, the embodiments described herein allow significant flexibility to be achieved in the process of induction cooking. The cooking vessel may be non-ferrous and in any of a variety of shapes, including a cylinder, cube, parallelepiped, or other shape. By virtue of using the embodiments described herein, the cooking vessel does not need to be made from a special and expensive cooking metal. Additionally, a household (or commercial) kitchen may have a large number of cooking vessels that may be made of, for example, a heat resistant plastic. In one embodiment, these heat resistant plastic cooking vessels may be stackable and/or partially foldable. By virtue of using the embodiments described herein, foods cooked in such heat resistant plastic containers may be refrigerated or frozen in the same container in which the food is cooked (e.g., using the ferrous cooking covers described above). There is no need to transfer the food from a ferrous cooking pot to a different container, which is the norm in conventional cooking methods, thereby simplifying not only cooking, but also food storage, while reducing the numbers of dishes that need to be cleaned after cooking.

As discussed above, the cooking vessels described herein may be of various shapes and sizes, and may be formed of a heat resistant glass, plastic, or wood, for example. Other non-ferrous materials may also be used. In at least some embodiments, the cooking vessels may in fact include certain ferrous portions (e.g., incorporated within the cooking vessel during production). In other embodiments, existing non-ferrous cooking vessels may be transformed into induction heat suitable cooking vessels, as discussed below. The transformation of a cooking vessel unsuitable for induction cooking into a cooking vessel suitable for induction cooking may be achieved in a variety of ways. For example, in one embodiment, the cooking vessel may be configured to receive induction heating elements (e.g., ferrous pieces) at a plurality of different locations in and around the cooking vessel. In these cases, the walls of the cooking vessel may receive induction heating elements via hooks or other attachment mechanisms. The cooking vessel may also receive the induction heating elements through one or more openings and/or compartments in a wall of the cooking vessel.

Specifically referring now to FIGS. 7A and 7B, a cooking vessel 700 includes induction heating elements 710, in accordance with at least some embodiments of the present disclosure. The induction heating elements 710, in at least some embodiments, are mounted to a wall of the cooking vessel 700. Furthermore, in at least some embodiments, the induction heating elements 710 may be mounted to the wall of the cooking vessel 700 via hooks or any other attachment mechanism. Furthermore, the induction heating elements 710 may be permanently or detachably mounted to the wall of the cooking vessel 700.

Notwithstanding the fact that the induction heating elements 710 have been shown in FIGS. 7A and 7B on only one wall of the cooking vessel 700, this is merely exemplary. In other embodiments, the induction heating elements 710 may be mounted to more than one wall of the cooking vessel 700. Furthermore, the number of the induction heating elements 710 that may be mounted to one or more walls of the cooking vessel 700 may vary from one embodiment to another depending upon the heating profile that is desired. Likewise, the shape, size, thickness, positioning, and angular orientation of the induction heating elements 710 may vary. Additionally, the induction heating elements 710 may be mounted to an interior wall of the cooking vessel 700 or alternatively or additionally, the induction heating elements may be mounted to an exterior wall of the cooking vessel.

In at least some embodiments, the cooking vessel 700 also includes slots 720 through which additional induction heating elements may be added to the cooking vessel to customize the heating profile of the cooking vessel. FIG. 7A illustrates two such induction heating slots, however, fewer or additional slots may be used in alternative embodiments. Also and similar to the induction heating elements 710, while the slots 720 have been shown on only one wall of the cooking vessel 700, in other embodiments, the slots may be provided one multiple walls of the cooking vessel to tailor the heating profile of the cooking vessel. Additionally, the placement, orientation, shape, and size of the slots 720 may differ in alternative embodiments.

In one embodiment, the slots 720 may be openings in a wall of the cooking vessel 700 into which induction heating elements may be placed into direct contact with the contents of the cooking vessel. The induction heating elements may be received within the openings of the slots 720 in any of a variety of ways that may be suitable. In some embodiments, the openings in the wall may include a door or other closable member to receive the induction heating elements. The slots 720 may, in some embodiments, also include notches in which the induction heating elements may be removably attached. In other embodiments, the slots 720 may be designed as compartments, which hold the induction heating elements. Doors may similarly be used to close the compartments such that the induction heating elements do not fall out if the cooking vessel 700 is moved. The induction heating elements may also be mounted via hooks or other attachment mechanisms in some embodiments. A combination of methods discussed above or other methods may be used to secure the induction heating elements. The embodiment of FIG. 7A depicts the slots 720 without induction heating elements. FIG. 7B depicts induction heating elements 730 placed into the slots 720.

As discussed above, "induction heating elements" pieces of metal subject to heating by induction, inserted or removed from a non-ferrous cooking vessel to enable heating to take place in a targeted and controlled manner. Specifically and as discussed in greater detail above, the "induction heating elements" may be composed of a material that may facilitate heating of the "induction heating elements" using an electromagnetic radiation source. Depending upon the application for which the "induction heating elements" are used, the "induction heating elements" may be designed to be suitable for that application. For example, if the "induction heating elements" are used for induction cooking, then the "induction heating elements" may be composed of a material or be positioned in a manner that is suitable for cooking and for being around food safely without poisoning the food.

Furthermore, in at least some embodiments, the same induction heating element(s) that are used to cook the food may be allowed to remain in the cooking vessel when the leftover food is refrigerated or frozen. When the food is to be reheated, the cooking vessel and induction heating element(s) may be simply placed on an induction stove (or other electromagnetic radiation source) for the radiation to heat the induction heating element(s), thereby reheating the food without the need to transfer the food from one container to another. The container in which the food is stored can be non-ferrous container such as coated cardboard. The user therefore does not have to utilize a cooking vessel that may be needed for other food preparation purposes in order to have this convenience.

Again and discussed above, the shape, size, and material of the cooking vessel 700 may vary from one embodiment to another. Additionally, the cooking vessel 700 need not always be a container type vessel. In at least some embodiments, the cooking vessel 700 may be a pan, bowl, or other type of non-ferrous vessel, or a tray as discussed in FIG. 8 below. Further, while not shown, the cooking vessel 700 may include one or more handles, as well as other features (e.g., venting holes) that cooking vessels typically have. Additionally, the cooking vessel 700 may have suspended induction heating element(s) within the cooking vessel, such as those discussed in FIGS. 1A and 1B above.

Figure 8:
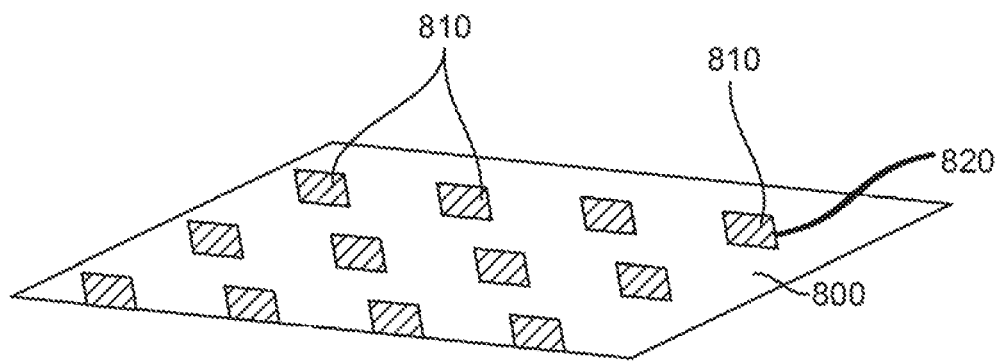
FIG. 8 depicts an induction smoker tray as a non-ferrous platform with induction heating elements placed in a desired pattern such that heat is generated via the induction heating elements in the desired pattern, in accordance with at least some embodiments of the present disclosure.

Turning now to FIG. 8, an induction smoker tray 800 is shown, in accordance with at least some embodiments of the present disclosure. The induction smoker tray 800 includes a plurality of receptacles 810 into which wood chips/pieces 820 may be placed. In one embodiment, the induction smoker tray 800 may be made of a non-ferrous material and the receptacles 810 may be made of a ferrous material, such that the wood chips/pieces 820 in the receptacles are heated with an electromagnetic heating source (not shown). Alternatively, the induction smoker tray 800 may be made of a ferrous material and the receptacles 810 may be made of a non-ferrous material. In yet another alternative embodiment, both the induction smoker tray 800 and the receptacles 810 may be made from a ferrous material or portions of the smoker tray and the receptacles may be made of a ferrous material with the remaining portions being made of a non-ferrous material. Upon application of electromagnetic radiation to the induction smoker tray 800, the wood chips/pieces 820 are heated to generate smoke, which may be used to cook and/or impart flavor onto food. The use of the receptacles 810 allows for selective heating (i.e., some receptacles may include wood chips/pieces and others may be left empty), which is not possible in a traditional flame based smoker.

Notwithstanding the fact that FIG. 8 shows the arrangement of the receptacles 810 in a certain way, this is merely exemplary. The shape, size, orientation, and placement of the receptacles 810 may vary from one embodiment to another. Likewise, while FIG. 8 has been described as having the wood chips/pieces 820 in the receptacles 810, in other embodiments, at least some of those receptacles may be filled with other types of materials such as flavor capsules, other foods, chemicals, etc. that impart a desired flavor to the food. Alternatively, at least a portion of the receptacles may be left empty.

Referring to FIGS. 9A and 9B, yet another type of a cooking vessel 900 is shown, in accordance with at least some embodiments of the present disclosure. The cooking vessel 900 includes an induction heating element 910. Similar to the cooking vessels discussed above, the cooking vessel 900 is composed of a non-ferrous material such that heat from an electromagnetic radiation source 920 is delivered to the contents of the cooking vessel through the induction heating element 910. In other embodiments, the cooking vessel 900 may be a combination of ferrous and non-ferrous material in which case, heat is delivered to the contents of the cooking vessel via the ferrous portions of the cooking vessel and the induction heating element 910. Again, the shape, size, configuration, and features of the cooking vessel 900 may vary from that shown in FIGS. 9A and 9B.

With respect to the induction heating element 910 in particular, it may be a mobile induction heating element capable of being positioned in a variety of positions. For example, FIG. 9A depicts the induction heating element 910 in a first orientation relative to both a wall of the cooking vessel 900 and to the electromagnetic radiation source 920. FIG. 9B depicts the induction heating element 910 in a second orientation relative to both the wall of the cooking vessel 900 and to the electromagnetic radiation source 920. While FIGS. 9A and 9B show two orientations of the induction heating element 910, various other orientations of the induction heating element are contemplated and considered within the scope of the present disclosure. In one embodiment, the induction heating element(s) can be automated and move by themselves such that the cook does not need to periodically stir the food. The motion of the induction heating elements will distribute heat through conduction and convection. Such automation can be achieved through the use of miniature servo-motors, through a controlled magnet, etc.

Additionally, in some embodiments, the induction heating element 910 is attached to the wall of the cooking vessel 900 via a hook and latch attachment (not shown) at an upper portion of the induction heating element that allows the induction heating element to rotate about a horizontal axis. As such, the induction heating element 910 is able to pivot from its position in FIG. 9A upward to the position shown in FIG. 9B and to many other configurations. In an alternative embodiment, the upper portion of the induction heating element 910 is secured to the wall of the cooking vessel 900 via a pivot rod or any other mechanism that allows the mobile induction heating element to pivot about an axis. While the description above describes motion of the induction heating element 910 about a horizontal axis, in at least some embodiments, the induction heating element may be configured to pivot about a vertical axis or at an angular axis, as may be deemed suitable. As mentioned above and discussed again below, the orientation of the induction heating element with respect to the electromagnetic radiation source may be varied to vary the heat intensity delivered by the induction heating element to the cooking vessel 900.

Furthermore, the orientation of the induction heating element 910 may be varied automatically by using a spring mechanism 930 attached to the induction heating element. The spring mechanism 930 includes a spring 940 attached to the induction heating element 910. In one embodiment, the spring mechanism 930 is configured to release the induction heating element 910 (e.g., to vary the orientation of the induction heating element) if a temperature in the cooking vessel 900 is, for example, less than a threshold temperature. The temperature in the cooking vessel 900 may be determined by a temperature sensor (not shown) in the cooking vessel, and the spring mechanism 930 may be automatically controlled by an actuator (also not shown) that is in communication with the temperature sensor. Upon receipt of a low temperature indication from the temperature sensor, the actuator may be configured to actuate the spring mechanism 930, which in turn may then move the induction heating element 910 from the orientation of FIG. 9A to the orientation of FIG. 9B or to another orientation until the threshold temperature is attained within the cooking vessel 900. Alternatively, the spring mechanism 930 may be manually operated to adjust the position of the induction heating element 910. In such an embodiment, the spring mechanism 930 also includes a handle, lever, etc. such that a user may use to manipulate the spring 940 and thereby adjust the induction heating element 910 into different orientations.

By virtue of adjusting the orientation of the induction heating element 910 with respect to the electromagnetic radiation source 920, the surface area of the induction heating element may be varied, thereby varying the heating intensity of the induction heating element. Specifically, the orientation of the induction heating element 910 relative to the electromagnetic radiation source 920 dictates the amount of heat generated by the induction heating element. For example, by orienting the induction heating element 910 into the position shown in FIG. 9B, more surface area of the induction heating element is directly exposed to the electromagnetic radiation that is emitted from the electromagnetic radiation source 920 located underneath the cooking vessel 900. Thus, the ability to manipulate the induction heating element 910 into different orientations enables a user to change the heating profile that is applied to the food and heat/cook the food more effectively and quickly. In at least some embodiments, the positioning, angle, and distance of the electromagnetic radiation source 920 relative to the induction heating element 910 may be varied to vary the heating profile.

Notwithstanding the specific embodiment described above in FIGS. 9A and 9B, variations are contemplated and considered within the scope of the present disclosure. For example, while the electromagnetic radiation source 920 has been described as being situated underneath the cooking vessel 900, in at least some embodiments, the electromagnetic radiation source may be located above and/or on one or more sides of the cooking vessel. Similarly, in other alternative embodiments, the spring mechanism 930 may be replaced by any other attachment mechanism that allows the induction heating element 910 to be manually or automatically moved into various orientations relative to the electromagnetic radiation source 920. Additionally, when the food is cooked and a given temperature is to be maintained, rather than increased, the spring mechanism 930 may be manually or automatically retracted such that the induction heating element 910 is no longer fully facing the electromagnetic radiation source 920. Automatic retraction of the spring mechanism 930 may be facilitated in the same manner as extending the spring mechanism by using the temperature sensor and the actuator.

Thus, by enabling the induction heating element 910 to be moved into a variety of orientations relative to the electromagnetic radiation source 920, the embodiments of FIGS. 9A and 9B allow the heat delivered to the contents of the cooking vessel 900 to be controlled based on the amount of surface area of the induction heating element 910 that is directly exposed to the electromagnetic radiation from the electromagnetic radiation source 920. Again, a larger exposed surface area generates more heat and, therefore, cooks food at a higher temperature, while a smaller exposed surface generated less heat and cooks food at a lower temperature. Also, while only one of the induction heating element 910 has been shown in FIGS. 9A and 9B, a plurality of such induction heating elements may be provided on one or more walls of the cooking vessel 900 controlled by one or an additional number of the spring mechanisms, temperature sensors, and actuators. Likewise, the size, shape, and placement of the induction heating element 910 may vary from one embodiment to another.

Figure 10B:
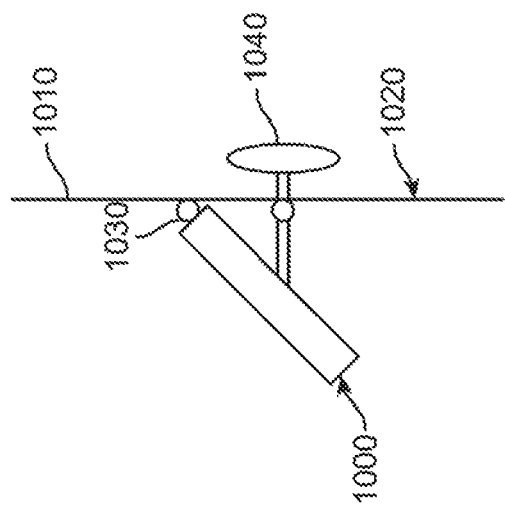
FIGS. 10A and 10B depict a cut-away view of a mobile induction heating element mounted on a wall of a non-ferrous cooking vessel, in accordance with at least some embodiments of the present disclosure.
Figure 10A:
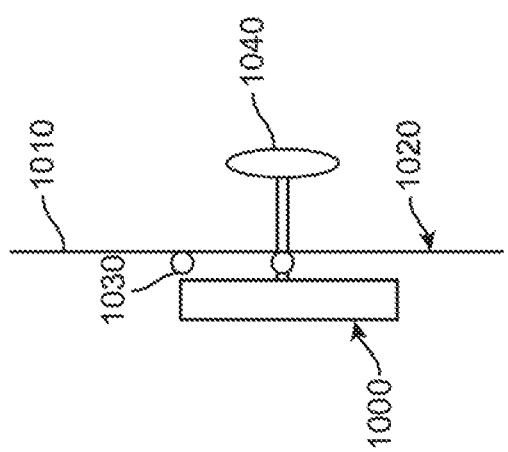

Turning now to FIGS. 10A and 10B, an alternate mechanism of varying the orientation of the induction heating element of FIGS. 9A and 9B is shown, in accordance with at least some embodiments of the present disclosure. Specifically, FIGS. 10A and 10B depict a cut-away view of an induction heating element 1000 mounted on a wall 1010 of a cooking vessel 1020, in accordance with at least some embodiments of the present disclosure. Only portions and features of the cooking vessel 1020 that are necessary for a proper understanding of the present embodiment are shown in FIGS. 10A and 10B. Nevertheless, as discussed with respect to FIGS. 9A and 9B above, the cooking vessel 1020 includes one or more temperature sensors, one or more actuators, and at least one electromagnetic radiation source for heating the induction heating element 1000. Likewise, while a single iteration of the induction heating element 1000 is shown in FIGS. 10A and 10B, multiple ones of the induction heating element may be provided on one or more walls of the cooking vessel 1020.

Similar to the embodiments of FIGS. 9A and 9B, the induction heating element 1000 is a mobile induction heating element capable of being oriented in varying positions relative to the electromagnetic radiation source, not shown. The induction heating element 1000 is attached to the wall 1010 of the cooking vessel 1020 via a hook and latch attachment 1030 at an upper portion of the mobile induction heating element. The hook and latch attachment 1030 allows the induction heating element 1000 to rotate about a horizontal axis. In the embodiments of FIGS. 10A and 10B, a screw 1040 is used to manipulate the induction heating element 1000 into a desired orientation. FIG. 10A illustrates the induction heating element 1000 in a retracted position, and FIG. 10B illustrates the induction heating element in a partially extended position. The screw 1040 may be manually or automatically manipulated, depending on the embodiment, in a manner similar to that described above in FIGS. 9A and 9B using the temperature sensor and the actuator.

In other embodiments, other mechanisms of controlling the orientation of the induction heating element 1000 may be used. For example, in some embodiments, instead of using the screw 1040, control of the induction heating element 1000 may be effected through a bimetallic strip, through an electronic arm in communication with a temperature (or other) sensor, etc. Furthermore, a combination of the mechanisms described above may be used within a single embodiment of the cooking vessel 1020.

Figure 11:
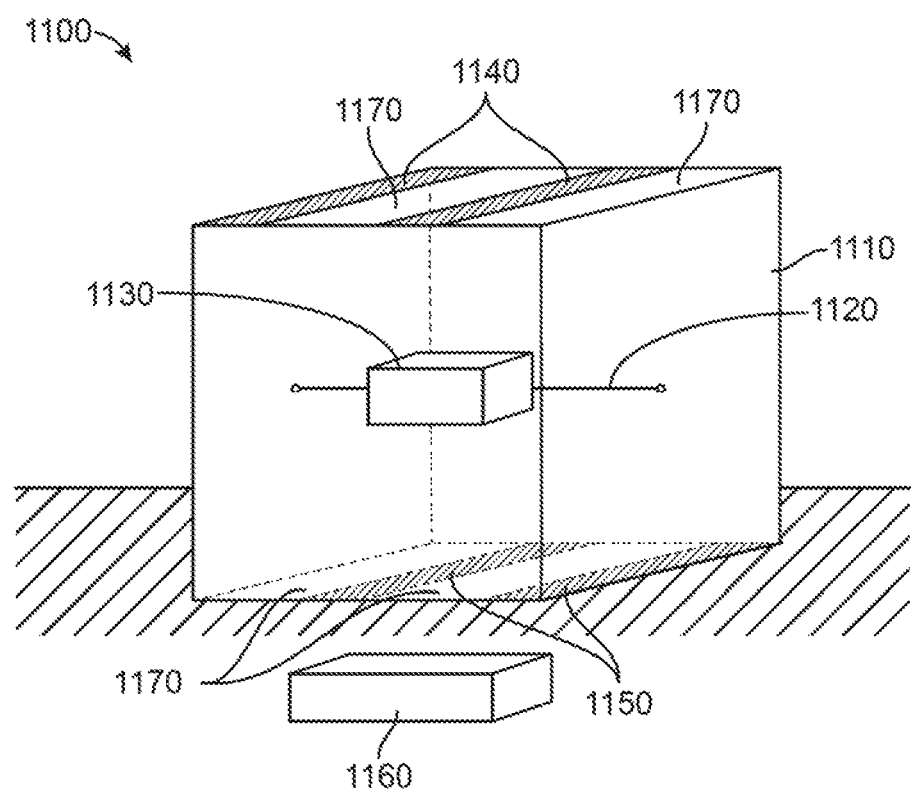
FIG. 11 depicts a cooking system having a non-ferrous cooking vessel comprised of a base and cover, with sections of each containing induction heating elements so that heating of food located between the base and cover takes place from the top and bottom, where the top and bottom elements are not in homologous position to enable electromagnetic radiation to pass through the base to the cover without interference (hereinafter 'induction cooking cage'), in accordance with at least some embodiments of the present disclosure.

Referring now to FIG. 11, yet another embodiment of a cooking vessel 1100 is shown, in accordance with at least some embodiments of the present disclosure. Specifically, the cooking vessel 1100 is configured as a cooking cage 1110 having a cooking bar 1120 upon which food 1130 may be skewered or otherwise secured for cooking. While the cooking bar 1120 has been shown as being secured or otherwise mounted to the side walls of the cooking cage 1110, in other embodiments, the cooking bar may assume other configurations. For example, in some embodiments, the cooking bar 1120 may extend upwardly or downwardly parallel or substantially parallel to the side walls of the cooking cage 1110. Likewise, the cooking bar 1120 need not always be a straight bar. The cooking bar 1120 may be curved, spiral, or assume other shapes and sizes to accommodate varying types of food items. In at least some embodiments, the cooking cage 1110 may be provided with a variety of combinations and configurations of cooking bars such that an appropriate one of the cooking bar 1120 may be used within the cooking cage depending upon the food that is to be cooked.

Additionally, the cooking bar 1120 may be stationary, or it may rotate, depending on the embodiment. In alternative embodiments, the cooking bar 1120 may be suspended in the cooking cage 1110 in a variety of ways, such as via hooks mounted to the cooking cage. Furthermore, in at least some embodiments, the walls of the cooking cage 1110 may be designed to expand and contract, either manually or electrically. In such embodiments, the walls of the cooking cage 1110 may be formed into an accordion shape that may be easily compressed to reduce the size of the cooking cage, or expanded to increase the size of the cooking cage. Alternatively, the cooking cage 1110 may have walls which slide horizontally into each other to further increase the flexibility of the cooking vessel 1100. With expandable or contractable configurations of the cooking cage 1110, the cooking bar 1120 may be configured to expand or contract as well. The cooking bar 1120 may be made to expand or contract in any of a variety of ways. For example, the cooking bar 1120 may be configured as portions of rods that slide within one another to vary the length thereof or the cooking bar may be made as an accordion structure itself, so it may be stretched or compressed as desired. Other mechanisms of varying the length of the cooking bar 1120 may be used in other embodiments.

Furthermore, in at least some embodiments, in addition to or instead of the cooking bar 1120, the food 1130 may be supported by a ferrous or non-ferrous food tray (not shown), depending on the amount of desired heat. Liquids may also be cooked in this way using the cooking cage 1110, and the cooking cage may be configured such that the liquid is heated from any desired direction. Foods and liquids may also be cooked together, and in some embodiments the food may be held in a non-ferrous container inside the cooking cage 1110 or in a heat resistant bag that may be flexible.

The cooking cage 1110 also includes upper ferrous strips 1140 secured or otherwise attached to an upper portion of the cooking cage. The upper ferrous strips 1140 are configured to generate heat and heat the food 1130 from the top. In addition to the upper ferrous strips 1140, in at least some embodiments, the cooking cage 1110 also includes lower ferrous strips 1150 that are secured or otherwise attached to a bottom portion of the cooking cage for generating heat to heat the food 1130 from the bottom. The upper ferrous strips 1140 and the lower ferrous strips 1150 generate heat by virtue of receiving electromagnetic radiation from an electromagnetic radiation source 1160. In addition, the upper and lower ferrous strips are not homologous (i.e., the top and bottom strips do not line up with one another exactly). If the top and bottom strips were lined up exactly on top of one another, the electromagnetic radiation would be absorbed by the lower strips and would not reach the upper strips.

Similar to the cooking bar 1120, the upper ferrous strips 1140 and the lower ferrous strips 1150 may assume various different configurations. For example, the shape, size, thickness, angle, and orientation of each of the upper ferrous strips 1140 and each of the lower ferrous strips 1150 may vary from one embodiment to another, depending particularly upon the heating profile that is desired. Additionally, while in the present embodiment only two of the upper ferrous strips 1140 and two of the lower ferrous strips 1150 have been shown, this is merely exemplary. In other embodiments, more or less than two ferrous strips may be used in both the upper ferrous strips 1140 and the lower ferrous strips 1150. Furthermore, in at least some embodiments, additional ferrous strips may be provided on the side walls of the cooking cage 1110. The walls of the cooking cage 1110 are non-ferrous in at least some embodiments. The walls of the cooking cage 1110 may also include slots, brackets, etc. to hold the additional ferrous strips such that the food 1130 may be heated from the side.

Additionally, extendable heating elements (e.g., such as those described in FIGS. 1A and 1B above) may be provided within the cooking cage 1110 and/or a mobile induction heating element (such as those described in FIGS. 9A/9B and 10A/10B above) may be used. Moreover, in at least some embodiments, only either the upper ferrous strips 1140 or the lower ferrous strips 1150 may be used. Furthermore, in at least some embodiments, the upper ferrous strips 1140 and the lower ferrous strips 1150 may include a non-ferrous (or non-metallic) side that faces away from the food 1130, and a ferrous side that faces the food. In such an embodiment, the non-ferrous side may be clad with a heat resistant material. One or both of the upper ferrous strips 1140 and the lower ferrous strips 1150 may also include a non-ferrous lip, grip, protrusion, etc. such that the ferrous strips may be better handled when hot. Thus, a variety of configurations of the ferrous strips are contemplated and considered within the scope of the present disclosure. Additional handles to lift or move the cooking cage 1110 may be used as well in some embodiments.

In at least some embodiments, the cooking cage 1110 may be provided with cooking covers such as those described in FIGS. 1A-6 above. These cooking covers may be in addition to or instead of the upper ferrous strips 1140 and/or the lower ferrous strips 1150.

Furthermore, in at least some embodiments, the upper ferrous strips 1140 and the lower ferrous strips 1150 may be separated from one another by a non-ferrous material 1170. For example, in at least some embodiments in which the non-ferrous material 1170 is used, the non-ferrous material is placed between the upper ferrous strips 1140 such that the cooking cage 1110 has a solid top surface. Similarly, the non-ferrous material 1170 is placed between the lower ferrous strips 1150 such that the cooking cage 1110 has a solid bottom surface. In alternative embodiments, the top and/or bottom of the cooking cage 1110 may be at least partially open.

As discussed above, in embodiments in which a cage structure is used, the upper ferrous strips 1140 are offset (i.e., not directly on top of) relative to the lower ferrous strips 1150. By virtue of offsetting the upper ferrous strips 1140 from the lower ferrous strips 1150, electromagnetic radiation from the electromagnetic radiation source 1160 may pass in between the lower ferrous strips and make contact with the upper ferrous strips, thereby making the heating of the upper ferrous strips more effective.

Additionally, in one embodiment, the bottom of the cooking cage 1110 has a frame into which the lower ferrous strips 1150 any non-ferrous material 1170 are placed or secured. As discussed above, the non-ferrous material 1170 between the lower ferrous strips 1150 allows electromagnetic radiation to pass right through to the upper ferrous strips 1140 that are placed directly above the lower non-ferrous material and thereby offset from the lower ferrous strips. The upper ferrous strips 1140 may also be mounted in a frame at the top of the cooking cage 1110. Thus, by providing the upper ferrous strips 1140, the lower ferrous strips 1150, and the cooking bar 1120, the food 1130 may be effectively and quickly cooked within the cooking cage 1110.

Figure 12:
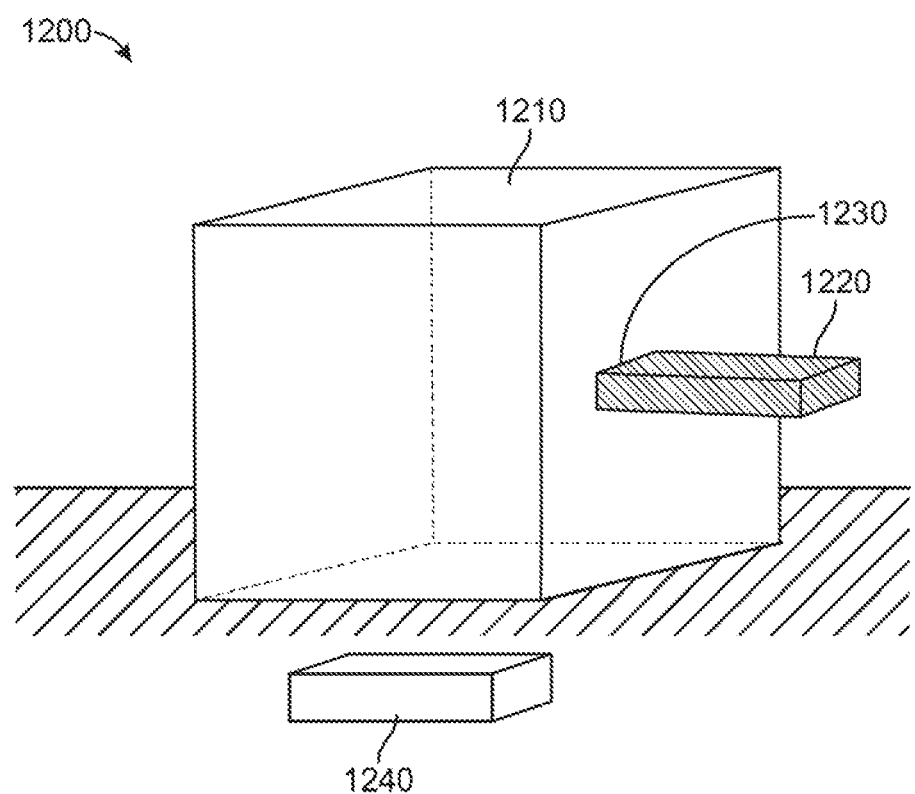
FIG. 12 depicts a cooking system having a cooking vessel with automated placement and insertion of induction heating elements, in accordance with at least some embodiments of the present disclosure.

Turning now to FIG. 12, an induction cooking system 1200 is shown, in accordance with at least some embodiments of the present disclosure. Specifically, the induction cooking system 1200 includes a non-ferrous cooking vessel 1210 having an automated placement of one or more induction heating elements 1220. The cooking vessel 1210 may be made partially or entirely from a non-ferrous material. In at least some embodiments, the induction heating elements 1220 are selectively inserted into the cooking system 1200 to provide more heat. The induction heating elements 1220 may be manually or automatically inserted into a slot 1230 in the wall of the cooking vessel 1210. In an embodiment in which the induction heating elements 1220 are automatically inserted, a temperature sensor (not shown) may be used in conjunction with an, also not shown, automatically controlled arm (or other actuator) that inserts/removes the induction heating elements based on a sensed temperature within the cooking system 1200.

For example, when inserted into the wall of the cooking vessel 1210, the induction heating elements 1220 may absorb electromagnetic radiation from an electromagnetic radiation source 1240 to increase a temperature of the cooking vessel based on a temperature reading that is below a desired value. Similarly, the induction heating elements 1220 may be removed from the cooking vessel 1210 to maintain a desired temperature or reduce the temperature if the temperature gets too high.

Notwithstanding the fact that in the present embodiment, a single one of the induction heating elements 1220 inserted into a single one of the slot 1230 has been shown, this is merely exemplary. Rather, in other embodiments, multiple smaller ones of the induction heating elements 1220 may be inserted into the slot 1230. Similarly, multiple numbers of the slot 1230 may be used in some embodiments, with each of the slots having one or more of the induction heating elements 1220. Likewise, the size, shape, angle, and orientation of the induction heating elements 1220 and the slot 1230 may vary in some embodiments as well. Also, while the slot 1230 and the induction heating elements 1220 have been shown on only one wall of the cooking vessel 1210, in at least some embodiments, slots and induction heating elements may be provided on multiple walls of the cooking vessel. Additionally, when multiple numbers of the slot 1230 holding multiple numbers of the induction heating elements 1220 are used, the size, shape, angle, and orientation of each of the induction heating element may vary to achieve the desired heating profile. Furthermore, in such cases, the insertion and removal of the induction heating elements 1220 may be either manual, automatic, or a combination of both. In some embodiments, additional heating elements and handles (such as those discussed in FIGS. 1A-1B) may be provided as well.

Thus, using the embodiments described herein, it is, again, apparent that a metal cooking vessel (e.g., ferrous cooking vessel) is no longer necessary to take advantage of induction cooking. Rather, non-ferrous containers and cooking vessels having automated and/or manual mobility aspects allow for much greater flexibility and control in induction cooking. Opening and closing of induction elements in the top or base of a container also allow for adding ingredients, placing ferrous and/or non-ferrous sections aside, etc. In addition, heating and then simmering, and other combinations, for example, become possible in the same container (i.e., while multiple containers are being heating via a single electromagnetic radiation source) without the need for multiple time-consuming transfers from one pot to another. Additionally, stirring while heating may become a simple automatic process since the non-ferrous container is more amenable to the addition of electrically controlled devices.

The embodiments described herein make possible targeted heating and cooking in a variety of circumstances outside of conventional food preparation. For example, a commercial food manufacturer may have a food product that consists of two or more distinct types of food, one or more of which are to be cooked and one or more of which are not to be cooked. Instead of preparing the foods separately and then packaging them in a multi-step process, the embodiments described herein make it possible to place ingredients/food into separate sections of a non-ferrous package, with the ingredients/food to be cooked in a compartment (or compartments) having a readily removable ferrous element attached thereto. Passing the package over an electromagnetic radiation source results in cooking of the desired food component(s), and not cooking the other food product(s). An assembly line of such packages may result in significant savings for the food manufacturer.

Figure 13:
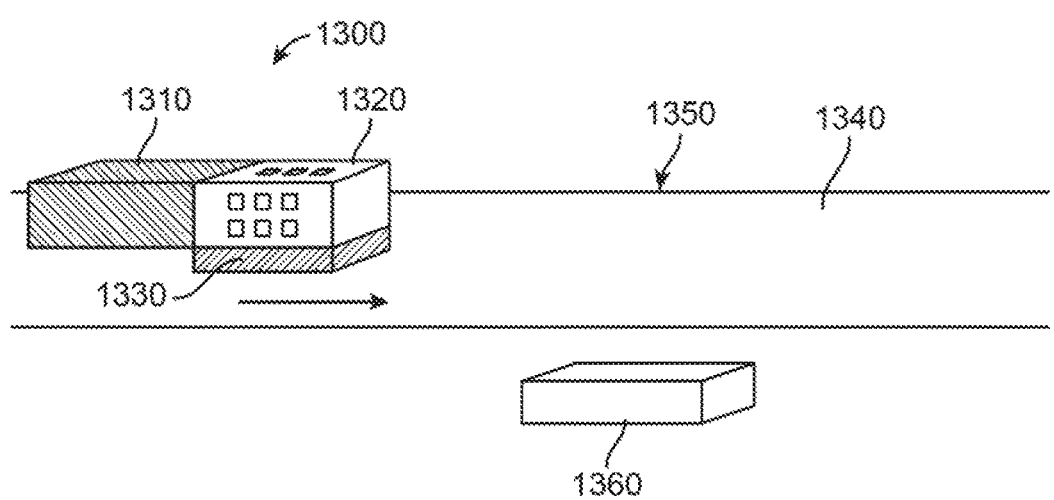
FIG. 13 depicts a multi-chamber cooking package, in accordance with at least some embodiments of the present disclosure.

Turning now to FIG. 13, a multi-chamber cooking package 1300 is shown, in accordance with at least some embodiments of the present disclosure. In at least some embodiments, the multi-chamber cooking package 1300 includes a first chamber 1310 that includes food which is not to be cooked, and a second chamber 1320 that includes food which is to be cooked. It is to be understood that although the multi-chamber cooking package 1300 has been shown as having only two chambers (e.g., the first chamber 1310 and the second chamber 1320), in other embodiments, the number of chambers may vary. Depending upon the number of chambers desired, the multi-chamber cooking package may have only a single chamber or possibly even greater than two chambers. Further, the shape and size of each chamber within the multi-chamber cooking package 1300 may vary from one embodiment to another. Likewise, the overall shape and size of the multi-chamber cooking package 1300 may vary as well.

For facilitating the cooking of food in the second chamber 1320, the second chamber includes an induction heating element 1330 attached or otherwise mounted thereto. In at least some embodiments, the induction heating element 1330 is detachable from the second chamber 1320 after the contents of the second chamber have been cooked. Notwithstanding the fact that in the present embodiment, a single one of the induction heating element 1330 has been shown attached/mounted to the second chamber 1320, in other embodiments, more than one of the induction heating elements may be provided on one or more walls of the second chamber. Furthermore, the shape, size, angle, and orientation of the induction heating element 1330 may vary from one embodiment to another. Also, while the induction heating element 1330 has been shown as being attached/mounted to an outer surface of the wall of the second chamber 1320, in some embodiments, the induction heating element may be mounted to an inner surface of the wall of the second chamber.

Moreover, in at least some embodiments, an induction heating element may be provided on the first chamber 1310 as well when the first chamber includes contents that are to be cooked. The shape, size, orientation, number, angle, and area of attaching/mounting the induction heating element on the first chamber 1310 may vary from one embodiment to another.

By virtue of providing the induction heating element 1330 on the second chamber 1320, as the multi-chamber cooking package 1300 travels down a conveyor belt 1340 of an assembly line 1350, the multi-chamber cooking package may be made to pass over (or under, or by) an electromagnetic radiation source 1360 that heats the induction heating element 1330, thereby cooking the contents of the second chamber 1320. In alternative embodiments, multiple electromagnetic radiation sources may be used at a number of different locations and orientations on the conveyor belt 1340 relative to the multi-chamber cooking package 1300 to achieve a desired heating profile. The electromagnetic radiation source 1360 may itself be mobile or stationary. Thus, in some embodiments, the multi-chamber cooking package 1300 may be positioned in at least some embodiments, stationary position, while the electromagnetic radiation source 1360 may move relative to the multi-chamber cooking package to cook contents within the multi-chamber cooking package.

Figure 14:
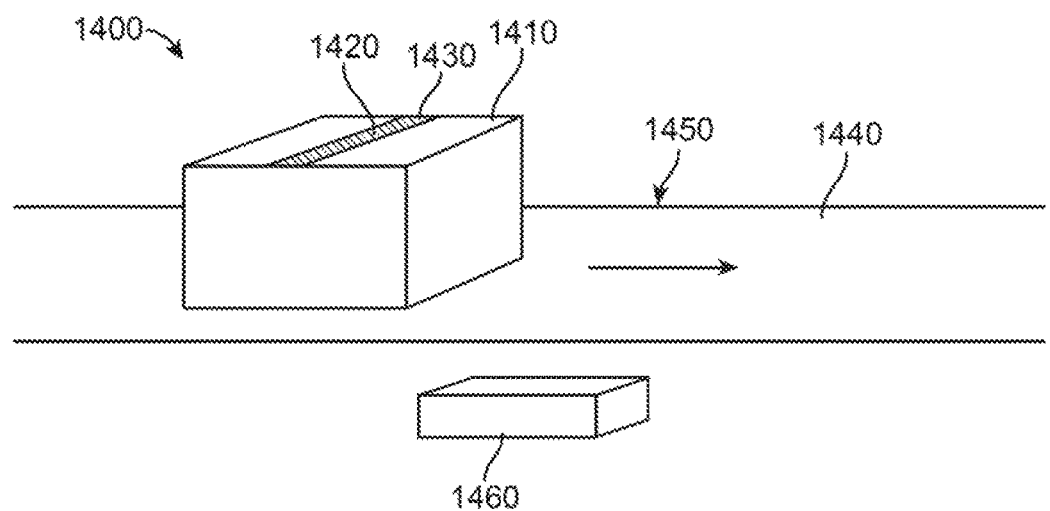
FIG. 14 depicts a system for sealing a package, container, parcel, etc. using induction heating, in accordance with at least some embodiments of the present disclosure.

The multi-chamber cooking package of FIG. 13 may be extended virtually in any manufacturing process (both cooking and non-cooking applications) in which heat is to be applied in a targeted manner. For example, FIG. 14 depicts a system 1400 for sealing a parcel 1410 using induction heating, in accordance with at least some embodiments of the present disclosure. The parcel 1410 can be a package, container, or other receptacle. In at least some embodiments, the parcel 1410 is not made of a ferrous material. Rather, the parcel 1410 includes a seam 1420 (or opening) that is to be sealed by a heat activated adhesive or plastic placed on the seam.

To seal the parcel 1410 using induction heating, an induction heating element 1430 is placed on the seam 1420 and particularly, over the heat activated adhesive or plastic on the seam. As the parcel 1410 moves along a conveyor belt 1440 of an assembly line 1450, the parcel passes through (e.g., over, under, or by) an electromagnetic radiation source 1460, which causes the induction heating element 1430 to heat up and melt/activate the heat activated adhesive or plastic on the seam 1420, thereby sealing the seam of the parcel.

As the parcel 1410 moves further down the conveyor belt 1440, the heat activated adhesive or plastic cools and hardens forming a permanent seal over the seam 1420. In at least some embodiments, the induction heating element 1430 may be removed from the seam 1420 to be re-used, or left on, depending on the implementation.

Notwithstanding the embodiment of the parcel 1410 shown in FIG. 14 above, many variations to the parcel are contemplated and considered within the scope of the present disclosure. For example, the shape and size of the parcel 1410 may vary. Likewise, the orientation of passing the parcel 1410 on the conveyor belt 1440 may vary. For example, while the present embodiment shows the parcel 1410 moving on the conveyor belt 1440 with the seam 1420 facing upward away from the conveyor belt, in other embodiments, the seam 1420 may be facing in other directions, including facing towards the conveyor belt. Also, the shape, size, and thickness of the seam 1420 may vary from one embodiment to another. Additionally, multiple numbers of the seam 1420, with each of the seams having an induction heating element thereon to seal the parcel 1410 may be used in other embodiments. Intentional gaps (e.g., for venting) may be left within the seam 1420 by strategically placing the induction heating element 1430 on the seam. Also, similar to FIG. 13, the electromagnetic radiation source 1460 may be stationary or mobile. It is to be understood that all items to be joined and sealed are non-ferrous in nature such that the electromagnetic radiation does not heat them as well.

The embodiments of FIGS. 13 and 14 may also be extended to an object that is to be glued/adhered in a particular spot with another object, or to any assembly line involving a spot or sector to be heated in a targeted manner. The processes may be used to adhere/connect both small and large objects. For example, a first body may need to be permanently adhered to a second body. Traditionally, such an operation would have been done by hand, with the first body lifted up, an adhesive, etc. applied to the first body, and first and second bodies brought into contact with one another to be secured. Nowadays, such an operation may be carried out by a number of complicated and expensive robotic machines. Even using modern machines, the first body must be lifted and, after the adhering/affixing operation takes place, replaced. In some circumstances, movement of the first body relative to the second body may be harmful to the contents and/or composition of the first body. Using the embodiments described herein, an induction heating element may be placed at an interface between the first body and the second body to enable the adhering/affixing process to take place in a predictable, controlled manner. Such a process is less costly than traditional methods and results in less disturbance to the first body, which is to affixed to the second body. The adhering process may be the result of using induction heat for fusing plastic surfaces to one another, activating a dry glue placed between the two surfaces, melting a solder between the two surfaces, etc. One such embodiment is described in FIG. 15 below.

Figure 15:
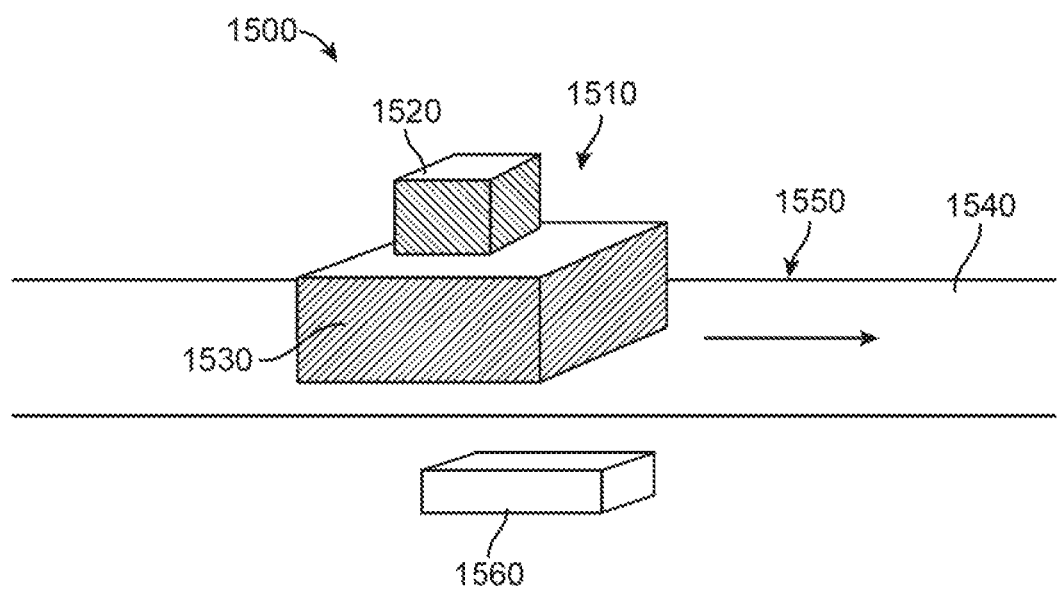
FIG. 15 depicts a system for assembling or attaching components of a product using induction heating, in accordance with at least some embodiments of the present disclosure.

Turning now to FIG. 15, a system 1500 for assembling components of a product 1510 using induction heating is shown, in accordance with at least some embodiments of the present disclosure. The product 1510 includes a first body 1520 that is to be attached to a second body 1530. An induction heating element (not visible) is placed at the interface between the first body 1520 and the second body 1530. Specifically, in some embodiments, the induction heating element is placed to cover only a portion of the interface, and the remainder of the interface is covered by an adhesive or other material such as glue, plastic, solder, etc. to facilitate the attachment of the first body 1520 to the second body 1530 at the interface. In other embodiments, the induction heating element is placed to cover substantially all of the interface between the first body 1520 and the second body 1530. The portion of the interface that is covered by the induction heating element may be dependent upon the shape, size, number, angle, and orientation of the induction heating element, as well as the shape and size of the first body 1520 and the second body 1530, and the type of adhesive/solder/plastic used in the interface to attach the first body to the second body.

By virtue of using the induction heating element, the first body 1520 may be attached to the second body 1530 using induction heat. Specifically, the product 1510 is moved down a conveyor belt 1540 of an assembly line 1550 and as the product passes through (e.g., over, under, or by) an electromagnetic radiation source 1560, the electromagnetic radiation source heats up the induction heating element. The heated induction heating element in turn melts/heats the adhesive or other material at the interface of the first body 1520 and the second body 1530 such that the first body is attached to the second body.

Again and as discussed in FIG. 14 above, variations to the product 1510, the first body 1520, the second body 1530, the conveyor belt 1540, and the induction heating element are contemplated and considered within the scope of the present disclosure. For example, the conveyor belt 1540 may be linear or non-linear (e.g., curved or circular), depending on the implementation. Furthermore, while the present disclosure has been described as having the first body 1520 and the second body 1530, in other embodiments, more than two components of the product 1510 may be attached using the disclosure herein. Furthermore, the embodiments of FIG. 15 may be extended to a multiplicity of affixing/adhering operations, to processes involving human and/or robotic actions, to different methods of controlling the movements, at a variety of speeds, etc.

Often it is necessary to add heat a glue joint to disassemble an object. The embodiments may also be used to sever connections between bodies in alternative embodiments. For example, two items held together by solder or glue can be separated by placing an induction element at the joint and training an electromagnetic source on the element. Such a process is much safer than a flame. Also, the electromagnetic radiation source 1560 may be mobile or stationary. For example, in one embodiment, the electromagnetic radiation source can be a handheld battery powered unit. As noted above, use of a flame is dangerous and can damage the object being disassembled. In practice, a ferrous heating element is placed adjacent to the joint or encompassing the joint. Placing the radiation source proximate to the joint will help to ensure that only the joint is heated. Should there be ferrous metal near the joint, the process can be modified to avoid heating the nearby ferrous metal. Specifically, a long ferrous heating element can be used, with one end of the long ferrous heating element touching or encompassing the joint and the other end of the long ferrous heating element proximate to the radiation source. In such an implementation, the radiation source is more distant from the joint and the radiation can be targeted to heat the far end of the heating element. The remainder of the heating element (including the portion in contact with the joint) will heat via conduction such that the joint be heated for disassembly. In general, the above approaches can be used whenever something has to be melted.

Figure 16:
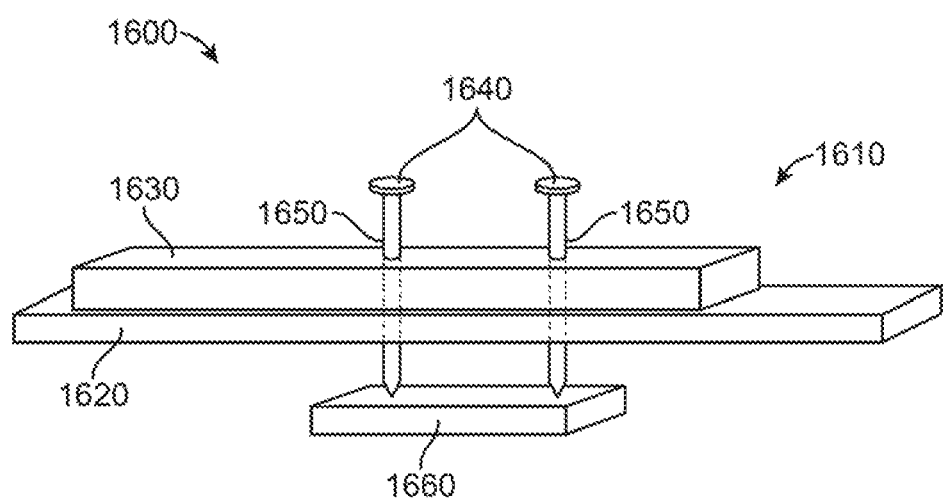
FIG. 16 depicts another system for assembling or attaching components of a product using induction heating, in accordance with at least some embodiments of the present disclosure.

Referring now to FIG. 16, another implementation of an affixing operation is shown, in accordance with at least some embodiments of the present disclosure. Specifically, the affixing operation of FIG. 16 includes a sheet of carbon fiber material to which a device made of hard plastic is to be affixed. Ferrous metal screws (or other fasteners) are placed into prepared holes/openings, and the product is passed by an electromagnetic radiation source that expands the screw, melts the plastic and carbon fiber, and creates a permanent interlocking interface between the carbon fiber material and the device. These concepts may be extended to implementations in which the product is on a conveyor belt, in which the product is stationary and the electromagnetic radiation source passes over, under, or by the product either manually or automatically, where the electromagnetic radiation source and/or the product are moved in accordance with a control program, etc. In another embodiment, the affixing operations can be used in the building industry in situations where one surface is to be affixed to another surface. For example, small heating elements can be placed together with heat activated adhesives or adhesives enclosed in readily melted capsules. When the two surfaces are in place, passing an electromagnetic source nearby will activate the adhesive and affix the surfaces. In one implementation, the radiation source can be attached to a drone which can easily traverse the area in a readily controlled manner.

Thus, FIG. 16 depicts another system 1600 of assembling components of a product 1610 using induction heat, in accordance with at least some embodiments of the present disclosure. The product 1610, in at least some embodiments, includes a carbon fiber component 1620 and a plastic component 1630 to be attached to the carbon fiber component. The shape, size, and orientation of one or both of the carbon fiber component 1620 and the plastic component 1630 may vary from one embodiment to another. Screws 1640 are placed into aligned holes 1650 in both the carbon fiber component 1620 and the plastic component 1630. Alternatively, other types of fasteners, rods, etc. other than the screws 1640 may be used. Further, the location, and orientation of the screws 1640 and the corresponding holes 1650 may vary from one embodiment to another depending upon the type of assembling that is desired. Additionally, although two of the screws 1640 are illustrated in FIG. 16, it should be understood that additional or fewer screws may be used in alternative embodiments.

Notwithstanding the fact that in the present embodiment, the carbon fiber component 1620 is shown as being assembled to the plastic component 1630, this is merely exemplary. Rather, in other embodiments, any type of components (of any type of non-ferrous material) that are to be assembled together using screws or other type of fasteners capable of being heated may benefit from the embodiments described herein.

Specifically, to assemble the carbon fiber component 1620 and the plastic component 1630 using the screws 1640, an electromagnetic radiation source 1660 is used. In at least some embodiments, the electromagnetic radiation source 1660 is positioned under the holes 1650 causing the screws 1640 to heat up. As the screws 1640 heat up from the electromagnetic radiation source 1660, the screws expand and melt a portion of the carbon fiber component 1620 and a portion of the plastic component 1630 surrounding the screws. The melting of the carbon fiber component 1620 and the plastic component 1630 causes the plastic component to be attached to both the screws 1640 and the carbon fiber component. The carbon fiber component 1620 is, likewise, attached to the screws 1640 and the plastic component 1630, thereby assembling the carbon fiber component and the plastic component together.

While the electromagnetic radiation source 1660 has been shown as being positioned under the carbon fiber component 1620 and specifically under the holes 1650, the positioning of the electromagnetic radiation source may vary in other embodiments. For example, the electromagnetic radiation source 1660 may be positioned over, at the sides of, or at an angle relative to the holes 1650. Additionally, the electromagnetic radiation source 1660 may be mobile or stationary (relative to the product 1610) depending on the embodiment and specifically, the heat profile that is desired and the location/orientation of the screws 1640. The product 1610 may also be mobile or stationary relative to the electromagnetic radiation source 1660. In at least some other embodiments, one or more additional induction heating elements (i.e., in addition to the screws 1640) may be used to assist in melting the materials (e.g., the carbon fiber component 1620 and the plastic component 1630) together. Further, although not shown, one or both of the product 1610 and the electromagnetic radiation source 1660 may be positioned on a conveyor belt.

Figure 17A:
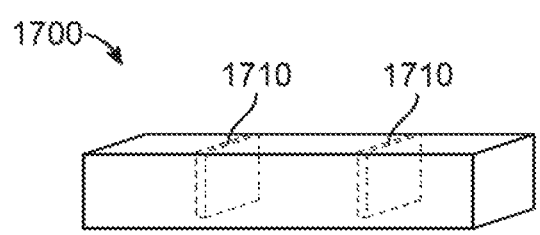
FIGS. 17A and 17B depict a food packaging system with integrated induction elements, in accordance with at least some embodiments of the present disclosure.
Figure 17B:
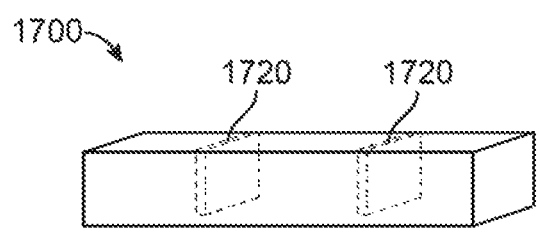

In addition to connecting or assembling components together, the embodiments described herein may also be used for food packaging. Specifically, the use of food packaging as an integral part of the heating/cooking process becomes possible using the embodiments described herein. Referring specifically to FIGS. 17A and 17B, a food packaging system 1700 is shown, in accordance with at least some embodiments of the present disclosure. While the food packaging system 1700 is shown as a rectangular box in FIG. 17, it is to be understood that different shapes, sizes, and configurations of food packaging are also envisioned. In at least some embodiments, the food packaging system 1700 includes built in slots 1710 (FIG. 17A) into which induction heating elements 1720 (FIG. 17B) are inserted. Specifically, the food packaging system 1700 has the slots 1710 into which the induction heating elements 1720 may be placed by a purchaser/user of the food packaging system 1700 to heat/cook the food therein. It is to be understood that although only two of the slots 1710 are shown in FIG. 17A, additional or fewer slots may be used in other embodiments, with each of the slots being designed to receive one or more of the induction heating elements 1720. The slots 1710 may also vary in size and/or shape.

The slots 1710 may be configured to receive a standard sized induction heating element (e.g., the induction heating elements 1720) or other piece of ferrous metal such that the food may be heated/cooked right in the package in which the food is purchased. As a result, the food may be conveniently cooked by placing the food packaging system 1700 on an induction cooktop (or other electromagnetic radiation source). In at least some embodiments, the food packaging system 1700 is made from a non-ferrous heat resistant material. In one embodiment, the food packaging system 1700 (as purchased) may include the induction heating elements 1720 in or around the packaging system such that the user does not have to place the induction heating elements into the food packaging system. In another embodiment, through placement of the induction heating elements 1720, only a portion of the food in the food packaging system 1700 is heated at a time, and the remaining food may be left in the food packaging system and placed in the refrigerator until the remaining food is to be reheated. This may all be done without removing the food from the food packaging system or needing to transfer to a pot to cook the food in. In another embodiment, the food packaging system 1700 itself may acts as a cooking vessel. For example, the food packaging system 1700 may include a dry food product which is to be cooked in water. Water may be added to the food packaging system 1700 and the food packaging system may be placed on an induction stove (or other electromagnetic radiation source) such that electromagnetic radiation heats one or more induction heating elements in or around the food packaging.

Figure 18A:
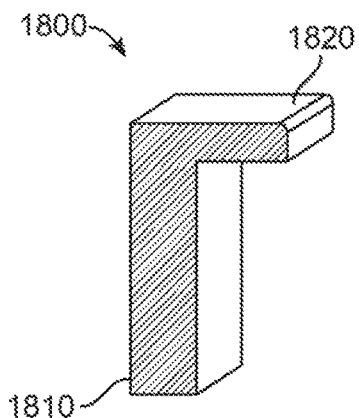
FIGS. 18A-18C depict induction elements having non-inductive portions, in accordance with at least some embodiments of the present disclosure.
Figure 18B:
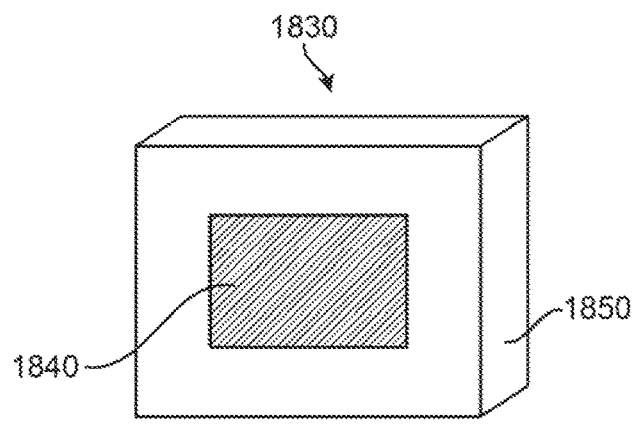
Figure 18C:
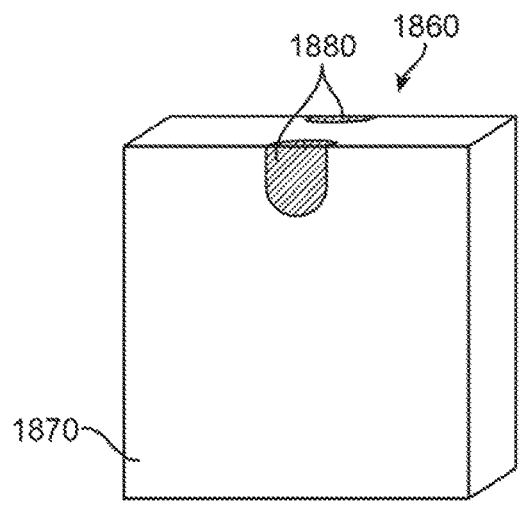

In at least some embodiments, the induction heating elements 1720 (and other induction heating elements described in this disclosure) may include a non-ferrous portion that does not get directly heated as a result of receiving electromagnetic radiation. The non-ferrous portion may be used to handle/remove an induction heating element that is hot. The non-ferrous portion may be made of ceramic or another heat resistant material, and may be in the form of a lip, an edge, a grip, a handle, etc. FIGS. 18A-18C depict exemplary induction heating elements having non-ferrous portions, in accordance with at least some embodiments of the present disclosure.

Specifically, FIG. 18A depicts an induction heating element 1800 having a ferrous portion 1810 and a non-ferrous lip 1820 that may be used to handle the induction heating element when the ferrous portion 1810 is hot. FIG. 18B depicts an induction heating element 1830 having a ferrous portion 1840 and a non-ferrous edge 1850 surrounding at least a portion of the ferrous portion such that the non-ferrous edge may be used to handle the induction heating element when the ferrous portion is hot. FIG. 18C depicts an induction heating element 1860 having a ferrous portion 1870 and non-ferrous grips 1880 (only one of which is visible in FIG. 18C) that may be used to handle the induction heating element when the ferrous portion is hot. While only a single one of the non-ferrous grips 1880 is visible in FIG. 18C, it is envisioned that the induction heating element 1860 includes at least a second one of the grips opposite the illustrated grip. In alternative embodiments, additional number of the non-ferrous grips 1880 may be used.

It is to be understood that while the induction heating elements 1800, 1830, and 1860 have been shown and described as having a certain configuration, this is merely exemplary. In other embodiments, the proportion of the ferrous portion relative to the non-ferrous portion may vary in the induction heating elements. Likewise, the shape and size of the induction heating elements may vary from one embodiment to another depending upon what is desired.

Additionally, the type of the non-ferrous portion (e.g., the non-inductive lip 1820, the non-inductive edge 1850, and the non-inductive grips 1880) may vary from one embodiment to another. For example, the induction heating element 1800 of FIG. 18A may be configured with the non-inductive edge 1850 in addition to or instead of the non-inductive lip 1820. Thus, more than one type of non-ferrous portions may be used in any embodiment of the induction heating element. Furthermore, only three types of the non-ferrous portions have been described herein. Rather, in other embodiments, various other configurations of the non-ferrous portions, such as handles, rims, notches, etc., are contemplated.

Turning now to FIGS. 19A-19D, circuit switches 1900 are shown, in accordance with at least some embodiments of the present disclosure. As will be described further below, the circuit switches 1900 are triggered by an electromagnetic radiation source. Specifically, in at least some embodiments, a bimetallic strip is used to implement controls in conjunction with the electromagnetic radiation source.

To use the bimetallic strip to control the circuit switches 1900, in at least some embodiments, at least a portion of the bimetallic strip is configured to bend in a predetermined direction in response to being heating by the electromagnetic radiation source. Bending in the predetermined direction may result in the bimetallic strip going from a linear state to a curved state, or from a curved state to a linear state, depending on the implementation. Such bending of the bimetallic strip may open/close an electrical circuit in response to application/removal of the electromagnetic radiation source heating the bimetallic strip (which heats up in the presence of this radiation) or removing the source of heat. This will turn the circuit switches 1900 on or off as desired.

Furthermore, the electromagnetic radiation source may be remotely controlled such that the bending of the bimetallic switch may be remotely controlled and the switch (e.g., the circuit switches 1900) may be turned on/off from a remote location. This adds flexibility to the ability to control the flow of current in a circuit. The on/off feature enables the control of all fluid motion. The use of targeted electromagnetic radiation (as opposed to relying solely on ambient temperature to enact a change in the bimetallic strip) greatly expands the utility of such bimetallic strips and enables the use of smaller versions, while demonstrating the bending effect as a result of temperature changes.

Thus, FIGS. 19A and 19B depict a first circuit 1910 having a bimetallic strip 1920 that acts a switch for the first circuit. In the embodiment of FIG. 19A, the bimetallic strip 1920 is cool (or otherwise not heated by an electromagnetic radiation source 1930 (see FIG. 19B)), resulting in the bimetallic strip having a linear (e.g., straight or non-curved) shape that results in the first circuit 1910 being closed or on (i.e., current may flow through the first circuit 1910 because the bimetallic strip 1920 completes the first circuit). In FIG. 19B, the electromagnetic radiation source 1930 is used to apply electromagnetic radiation to the bimetallic strip 1920. As a result, the bimetallic strip 1920 becomes heated and temporarily assumes a non-linear (e.g., curved) shape, which results in an open circuit such that current cannot flow through the first circuit 1910 (i.e., the first circuit is off). The electromagnetic radiation source 1930 may be remotely or locally controlled, depending on the implementation. Thus, by virtue of using induction heat to control the bending of the bimetallic strip 1920, the circuit switch formed by the first circuit 1910 may be controlled.

FIGS. 19C and 19D depict a second circuit 1940 having a bimetallic strip 1950 that acts a switch for the second circuit. In the embodiment of FIG. 19C, the bimetallic strip 1950 is cool (or otherwise not heated by an electromagnetic radiation source 1960), resulting in the bimetallic strip having a linear shape that results in the second circuit 1940 being off (i.e., current does not flow through the second circuit because the position of the bimetallic strip results in an open circuit). On the other hand, in FIG. 19D, the electromagnetic radiation source 1960 is used to apply electromagnetic radiation to the bimetallic strip 1950. As a result, the bimetallic strip 1950 gets heated up and assumes a non-linear shape which results in a closed circuit such that current flows through the second circuit 1940 (i.e., the circuit is on). The electromagnetic radiation source 1960 may be remotely or locally controlled, depending on the implementation, to remotely or locally control the operation of the switch formed by the second circuit 1940.

Thus, the bimetallic strips 1920 and 1950 may be used to activate or deactivate a switch. Although not discussed specifically, such a switch circuit may, in addition to the bimetallic strip, also include resistors, capacitors, battery sources, etc. Other electrical components, although not shown or discussed, may be provided in the circuit switches 1900 in other embodiments.

The targeted heating of a ferrous metal via induction heating may also be used to form a detector device. For example, in one embodiment, a package may claim to only include food or edible material. A detection system may be used to check the package for ferrous material that is being smuggled in the package or that otherwise inadvertently made its way into the package. If the package is placed near an electromagnetic radiation source, the package increases in temperature, thereby providing an indication that the package includes ferrous material. The increase in temperature may be detected directly by placing a temperature sensor on or near the package, or indirectly based on emitted infrared radiation from the package. Such a method may eliminate the use of an X-ray detector (and its associated harmful rays) in at least some detection scenarios.

Figure 20:
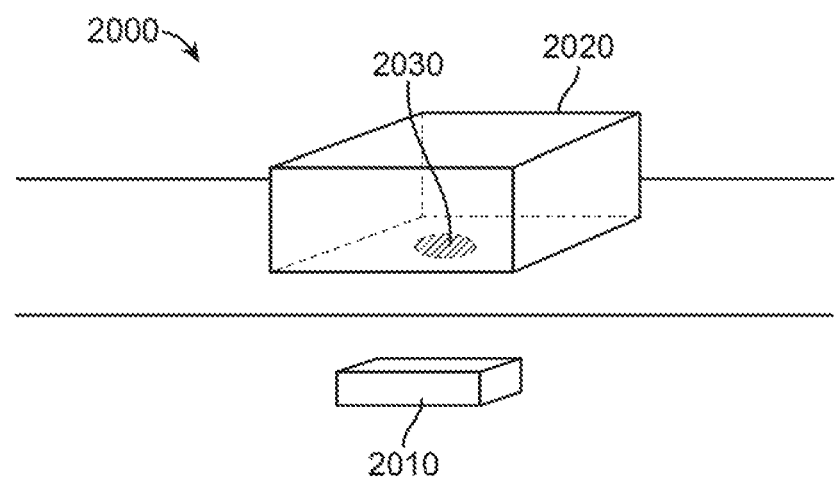
FIG. 20 depicts a system of detection based on induction heating, in accordance with at least some embodiments of the present disclosure.

To that end, FIG. 20 depicts a detection system 2000, in accordance with at least some embodiments of the present disclosure. The detection system 2000 includes an electromagnetic radiation source 2010 that is configured to emit radiation toward a package 2020. The package 2020 may be moving on a conveyor belt or may be stationary, depending on the implementation. Upon application of the electromagnetic radiation from the electromagnetic radiation source 2010, a piece of ferrous material 2030 inside the package 2020 generates heat, causing the package to increase in temperature and generate infrared radiation. A sensor, not shown, may be used to detect the increase in temperature and/or the infrared radiation. Upon detection of the heat/ infrared radiation and, assuming that the package 2020 is not supposed to contain any ferrous material, the detection system 2000 may generate a warning or alert to inform a user (e.g., inspector) that the package contains a piece of ferrous material (e.g., the ferrous material 2030) and may need further inspection.

Targeted induction heating may also be used to heat certain laboratory equipment used in experiments. Chemists, students, laboratory technicians, etc. often carry out experiments that require one or more contents of a test tube, flask, or other laboratory equipment to be heated. The contents of such equipment are traditionally heated by the chemist, student, lab technician, etc. holding the equipment over a Bunsen burner or other open flame. Use of such an open flame is dangerous, and may result in burns and/or unintentional fires. To improve safety, an induction heating element may be attached to or incorporated into the laboratory equipment.

For example, in one embodiment, an induction heating element may be implanted into the glass of the test tube, flask, or other laboratory equipment during production. Upon application of electromagnetic radiation, the implanted induction heating element heats the contents of the test tube, flask, or the other laboratory equipment safely without the need of a dangerous open flame.

Figure 21:
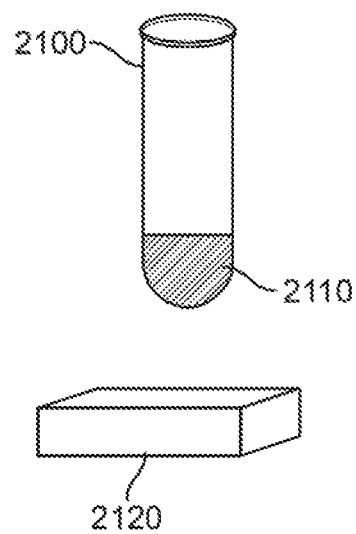
FIG. 21 depicts a test tube with an induction heating element, in accordance with at least some embodiments of the present disclosure.

Thus, FIG. 21 depicts a test tube 2100 with an induction heating element 2110, in accordance with at least some embodiments of the present disclosure. An electromagnetic radiation source 2120 generates electromagnetic radiation, which heats the induction heating element 2110 of the test tube 2100, thereby heating the contents of the test tube. The induction heating element 2110 may be attached to a surface of the test tube 2100 (i.e., post production), or incorporated into the test tube during production. While the embodiment of FIG. 21 illustrates the induction heating element 2110 on only an end portion of the test tube 2100, it is to be understood that the induction heating element 2110 may cover more (including the entire test tube) or less of the test tube, depending on the desired amount of heat desired. In one embodiment, a user may attach a desired number of induction heating elements to the test tube 2100 depending on a desired temperature to which the contents are to be heated.

Also, while FIG. 21 only shows the application of a test tube, other laboratory equipment that are to be heated are contemplated and considered within the scope of the present disclosure. For example, flasks, beakers, crucibles, cylinders, evaporating dishes, bottles, jars, etc. may benefit from the embodiments described herein.

Targeted induction heating may be used in a variety of other embodiments as well. Some of those embodiments are described below. For example, a narrow, targeted beam of electromagnetic radiation may also be used in colder climates to warm a car battery or other portion of a vehicle to facilitate easier starting of the vehicle. Specifically, a targeted electromagnetic radiation source may be placed proximate to a ferrous material positioned adjacent to the car battery. By emitting electromagnetic radiation, the electromagnetic radiation source may cause the ferrous material to heat up, thereby warming the battery and allowing the vehicle to start. In at least some embodiments, the electromagnetic radiation source may be powered from a wall outlet or other power source remote from the vehicle. Alternatively, the electromagnetic radiation source may be powered by the car battery itself or by a secondary battery associated with the electromagnetic radiation source.

Another application of targeted induction heating may involve verification of the authenticity of an item, such as of an enclosed/sealed package/item (e.g., a pill bottle), to help combat fraudulent reproduction and copying. For example, to authenticate an enclosed item, a detection unit may be incorporated into the enclosed item. In at least some embodiments, the detection unit may be incorporated into a small, sealed chamber of the enclosed item. The detection unit may itself be a sealed unit having a dye, paint, stain, ink, or other marking material therein. The marking material may vary in color and consistency. The walls of the detection unit may be made of plastic and ferrous elements may be incorporated inside the plastic walls along with the marking material. Alternatively, at least a portion of the detection unit walls may be made from ferrous materials.

When the enclosed item is exposed to electromagnetic radiation from an electromagnetic radiation source, the ferrous materials in the detection unit heats up and melts the plastic portion(s) of the walls of the detection unit, releasing the marking material. The small, sealed chamber that forms part of the enclosed item and that contains the detection unit may be placed in an innocuous place within the enclosed item. The small, sealed chamber may also include a small viewing window such that an end user or the authorities are able to view the marking material when it is released in response to electromagnetic radiation, thereby verifying the authenticity of the enclosed item without having to break/tamper/specifically inspect the enclosed item. The viewing window may form at least a portion of an exterior wall of the enclosed item, in at least some embodiments.

Thus, an end user or authorities may activate the detection unit with electromagnetic radiation to verify the authenticity of the enclosed item without having to open the enclosed item. Specifically, a replica or knock off of the enclosed item is likely not to include the small, sealed chamber or the detection unit which includes the ferrous material and marking material that is to be released upon exposure to electromagnetic radiation. The location of the detection unit and/or color of the marking material will be provided from the manufacturer to the end user, such that the user knows where to look for the marking material and what color the marking material should be. If the marking material appears in the correct location and is the correct color, the user may be confident that the enclosed item is authentic, before opening the enclosed item.

Such an authenticating system may be used to combat the proliferation of counterfeit drugs. Any duplicate packaging may appear the same on the outside, but is likely not to have the embedded detection unit which releases the marking material. In one embodiment, the detection unit may be configured such that the opening of the enclosed item triggers the release of the marking material. For example, the detection unit holding the marking material may include a detachable lid that is connected (by a wire, etc.) to a lid of the enclosed item such that the lid of the detection unit is opened when the lid of the enclosed item is opened, thereby releasing the marking material. Thus, if the end user receives the enclosed item with the marking material already visible, the end user may be alerted that the enclosed item may have been tampered with.

These embodiments provide advantages over the use of conventional authenticity messages, which are visible only under ultraviolet (UV) light. Use of light activated messages to show authenticity is subject to unauthorized inspection by third parties without alerting the end user that the inspection was performed. In the disclosed embodiments, inspection via electromagnetic radiation by a third party is apparent to the end user because the marking material has become visible by an unauthorized inspection prior to the enclosed item being received by the end user. The embedded detection unit may also be used for identification, selection, and detection purposes, in addition to protecting against tampering and counterfeiting as discussed above. The embedded detection unit may be of a variety of shapes and sizes, and multiple embedded detection units may be used simultaneously in a single enclosed item. In addition, the walls of the detection unit may be formed from meltable materials other than plastic.

The embodiments described herein have a multitude of applications which improve both safety and convenience. The ability to heat objects without a flame decreases the likelihood of a fire and burns. The ability to specifically and effortlessly place heating elements in any location/orientation relative to food improves user convenience and cooking options. With recent advances in battery and other energy source technology, an induction cooktop or heating system may be made portable. Additionally, the embodiments described herein no longer require a user to heat a metal pot to heat contents of the pot. Rather, electromagnetic energy may be directed to one or more induction heating elements, which in turn act as the heat source for heating the contents of the pot.

Small, localized induction heating systems may be placed in hotel rooms, in workplace lunch rooms, in college dormitories, in parks, at rest areas, on hiking trails, in campgrounds, etc. Induction heating systems may also be plug in units and/or include batteries or other portable power sources, depending on the embodiment. The induction heating systems may be free of charge or pay to use units. Travelers, hikers, etc. may use the portable induction heating systems without the need to have a pot or other cooking container. Rather, the user may have (or be provided with) one or more induction heating elements that may be used to heat food in any number of containers. Turning on the electromagnetic radiation source of the induction heating system allows the food to cook without the risk of contamination from food of other users, as may happen, for example, when using a microwave oven. Microwave ovens also require cleaning and removal of food residue from previous users, and such maintenance is avoided with the user of the induction heating systems described herein. There is also low or no risk of fire when using a small, localized induction heating system.

Hospitals and other healthcare facilities may also use small, localized induction heating systems to warm up foods in a targeted and/or differential manner for the convenience of patients and staff. Caterers who are out on the road will similarly find convenience in the use of small, localized induction heating systems. Large quantities of food may be brought to a catered event, and a number of small induction heating systems may be used to carry out all of the heating operations needed to prepare and maintain a heated meal, with much less effort and a great deal more safety than in traditional preparation methods.

An induction heating system may also be added to a vehicle, such as a car, semi, truck, boat, all-terrain vehicle, etc. The engine and/or battery of the vehicle may act as a power source for the electromagnetic radiation source and the induction heating system may be used for cooking during outdoors events such as a tailgate party, picnic, etc. Additionally, the induction heating source may be used to generate heat in the vehicle for use in colder climates. This allows cooking and/or heating to be performed without the use of flames and dangerous fuels such as propane, lighter fluid, gasoline, etc.

The systems described herein may also be used in cold environments to heat articles of clothing. For example, an article of clothing may include ferric threads in at least a portion of the fabric. A layer of ferrous material can also be placed on one or more layers of non-ferrous material to form the cloth, or the cloth can be impregnated with ferrous particles (including ferrous nanoparticles). The ferrous particles can also be placed in paint, which can be applied to the cloth. Clothing can be formed from the cloth using standard procedures. Upon receipt of electromagnetic radiation, the ferric threads may generate heat, which is transferred to the wearer of the article of clothing. In alternative embodiments, induction heating elements other than ferric thread, such as ferric plates, ferric buttons, ferric fashion accessories, etc. may be incorporated on or into clothing to provide heat to the user. This allows the individual to not rely as much on dangerous space heaters, bonfires, etc. to stay warm. The electromagnetic radiation used to heat the induction clothing may come from a stationary source. Alternatively, as one example, vehicles may include electromagnetic sources that may activate the induction clothing from a distance as the vehicle passes by a wearer of the induction clothing. For example, construction workers, traffic officers, etc. may be able to heat themselves by utilizing electromagnetic radiation from passing vehicles. Similarly, such electromagnetic sources may be placed along sidewalks, trails, etc. such that passersby may be heated as they pass.

The systems described herein may also be used for cooking and/or heating during camping. For example, an induction heating source in conjunction with induction heating elements in a tent or other enclosing sleeping space is much safer that the use of gases such as propane, which may result in oxygen depletion and death. Thus, this may be applied to field use for both military personnel and civilians.

The systems described herein also provide for safer remote preparation of food. For example, a user may set a timer to have an induction hot plate begin heating inductive elements (which in turn heat food) while the user is on his/her way home from work. This process is safer than using electric cooktop, crock pot, or other electrical apparatus that may cause a fire when the user is not present. In one embodiment, a heat or temperature sensor may be incorporated into or placed near one or more of the induction heating elements. If the temperature sensor determines that the temperature exceeds a safe operating threshold temperature, the sensor may send a signal to cause the electromagnetic radiation source to shut down, thereby cooling the temperature of the heating element and reducing the risk of fire.

The systems described herein may also be used with robotic features for remote cooking or other applications using the robotic features. For example, a robotic arm may be incorporated into or near a refrigerator. The robotic arm may be configured to automatically take a container of food from the refrigerator (at a predetermined time) and place the food container near an induction heating system such that the food is heated. The robotic arm may also be configured to place induction heating elements into the food container. Alternatively, the food container may come with the induction heating elements already therein, or the user may place the induction heating elements in the food container in advance. As such, the food may remain cold for most of the day, but may be heated while the user is on his/her way home such the user comes home to a heated meal.

In one embodiment, the induction cooking system may be incorporated into an insulated portion of the refrigerator, and the robotic arm may move the food from a cold storage portion of the refrigerator into the insulated portion of the refrigerator at a predetermined time. The robotic arm (or other associated computing system) may then activate an electromagnetic radiation source such that the food in the insulated portion of the refrigerator is heated, allowing the user to come home to a hot meal that is already prepared. Again, the robotic arm may position induction heating elements in or around the food container and/or the insulated portion of the refrigerator. Alternatively, the induction heating elements may be placed by the user.

In another embodiment, a spoon or other utensil fashioned out of ferrous metal can serve as the heating element. A non-ferrous food container of appropriate size is placed adjacent to or on top of the electromagnetic source. When the spoon is placed in the container and the radiation source turned on, the metal of the spoon heats up, thereby causing the food in the container to heat up. In one configuration, the handle of the spoon is made of non-ferrous material such as wood, plastic, or ceramic such that the handle can be held without being burned. This concept is readily extended to other utensils of various sizes. In alternative embodiments, the utensil can be made entirely of metal which will heat up in the presence of the electromagnetic radiation. In another alternative embodiment, the utensil can be made from sections of ferrous metal in a substrate of non-ferrous material, or any other combination.

In another embodiment, a ferrous heating element can be placed in the wall of a non-ferrous food container such that at least a portion of the ferrous heating element is external to the food container and at least a portion of the ferrous heating element is internal to the food container. Placing the radiation source outside of the container will result in the exterior portion of the heating element quickly heating up, thereby heating the interior portion of the heating element via conduction such that the contents of the food container are heated. Any number of such heating elements can be used, in different areas of the container, and the heating elements can be of different sizes. The heating elements can be permanently mounted to the food container in one implementation. Alternatively, the heating elements can be adjustable such that the amount of the heating element which is internal/external to the food container can be altered by sliding the heating element further into (or out of) the food container. The heating elements may also be entirely removable from the food container. In such an embodiment, a plug component can be used to fill the hole which was previously occupied by a removed heating element.

In current practice, following the path of physical/chemical processes in a living animal or plant (such as blood or other fluid flow) is difficult and often involves the use of radioactive tracers, fluorescent molecules, etc. In another embodiment, dietary or other iron may be injected into the blood stream or other fluid path of a living entity and, upon being subject to electromagnetic radiation, the injected iron generates a safe level of heat. One or more heat detectors may be placed on or near the subject to identify areas of the subject that are being heated as a result of the injected iron. The one or more heat detectors are associated with a processing device that receives indications of detected heat and tracks the progression or location of the injected iron in the subject based on the detected heat. As a result, ongoing processes in living things may be followed without the need for radioactive tracking systems that are in current use.

The induction systems described herein may also be used for internal detection. For example, an induction technique may be used to detect the presence of (ferrous) shrapnel in an injured soldier. Specifically, electromagnetic radiation may be targeted to an injury site and heat detectors may be placed on/near the patient to determine whether there is an increase in heat due to the shrapnel within the patient. Additionally, it has been established that at least some bacterial infections involve the cooperation of bacteria to grow and form a large bacterial infection site, as opposed to remaining a collection of individual bacteria particles spread throughout an organism. Iron is an important component of bacterial growth. As such, an induction system may be used to pinpoint regions of bacterial infection. Specifically, electromagnetic radiation may be passed through an area of an organism such that iron in a bacterial infection emanates heat. Heat detectors may then be used to identify areas emanating heat to pinpoint the location of the infection.

The induction systems described herein may also be used to study animal learning. Current tests that explore animal learning capabilities often involve the imposition of hunger on the animal with the utilization of food as a reward for performing some task such as completing a maze. Induction heating elements may similarly be used to study animal learning. For example, an animal may be placed into a cage in a cold environment, where a portion of the cage is made of ferrous material that generates heat when subjected to an electromagnetic radiation. The cage may include the ferrous material in the form of spaced out strips of metal that may be moved around by the animal. As an example, the spaced out strips of metal may be in a portion of a roof of the cage and observers may determine how long it takes the animal to realize that it receives heat if it stands proximate to the spaced out strips. Observers may also determine whether the animal has the intelligence to manipulate the strips (i.e., move them all together into a single unit) to increase the heat in a given area of the cage, etc. Observers may also determine whether one animal is capable of teaching another animal how to manipulate the metal strips for a warming effect.

The embodiments described herein make it possible to create heat in a desired and targeted location without the use of convection, conduction, or heat radiation. Rather, electromagnetic radiation, which passes through tissue, food, plant matter, plastics, and non-ferrous metal, may be used to heat ferrous metal placed in the location of choice. The ferrous metal may have any shape, dimension, or state, including solid or liquid. The heating of the ferrous metal may be completely controlled for purposes of schedule, duration, repetition, and number of events for a given time period. Further, the level of heating may be modulated by the nature of the electromagnetic radiation sent by the electromagnetic radiation source. This enables the control and function at a distance not possible in the past.

The techniques described herein may also be used to conduct targeted pinpoint heating in both living entities and inanimate objects. For example, placing a small amount of metal into an entity/object and then passing electromagnetic radiation through the metal may allow for selection, control, and in some instances, self-repair. This differential reception of electromagnetic radiation, which appears as heat may also be used to destroy unwanted tissue, or heal and revive other tissue as the case may be. For example, consider a device implanted in living tissue which on occasion requires a current flow, but not so often as to justify an implanted battery or complicated receiver. Such a device may be powered using induction heat by placing a thermocouple wire in a desired location, where one end of the thermocouple wire is surrounded by additional ferrous material. Passing electromagnetic radiation through the thermocouple wire induces a temperature gradient, which in turn generates the desired current to provide power to the device, to perform nerve stimulation/treatment, accelerate healing, etc.

In another embodiment and as discussed above, a bimetallic strip may be placed in a location which is not readily accessible and used to complete a circuit or interrupt a circuit, as discussed herein. Sending electromagnetic radiation at a desired time heats the bimetallic strip, causing it to bend and thereby control the circuit. This principle may also be extended to opening and closing a valve by heating it using induction heat by surrounding it with ferrous material and causing a desired expansion. Expansion of this kind may be used to control an enclosed fluid, which in turn may be used to direct the flow of other liquids. The same principle may be used to melt a fuse in a circuit in order to begin a function or operation, for example, to interrupt an ongoing circuit at a predetermined time. Heat applied at a distance may also be used to induce adhesion of heat reactive adhesive in an industrial setting, promote healing in a living body, and stimulate a repair that requires heat.

The danger of the inadvertent triggering of the induction devices described herein due to stray radiation is low. For example, many individuals wear and/or carry ferrous metal without having the metal heat up as a result of stray radiation in the environment. To implement the induction devices described herein, strong, precisely directed electromagnetic radiation is used. In rare circumstances, it may be desirable to implement protective measures on the induction devices to prevent the effect of stray radiation, as is done relative to pacemakers, for example.

There are many applications for the induction methods described herein, including use of a ferrous paper-like wrapper attached to an electromagnetic source to heat food in any location, including at a user's desk, in a kitchen or lunchroom, in a restaurant, etc. In the farming industry, the methods described herein may be used to prevent frost from damaging plants by placing ferrous material in or around plants and causing the ferrous material to selectively heat the plants by applying the appropriate amount of electromagnetic radiation. Induction heating may also be used in blankets, clothes, etc. to heat humans and animals.

As discussed throughout, the ability to transmit heat remotely without the need for conduction, convection, or heat radiation provides advantages relative to safety, and does not require the installation of wires to conduct electricity. Additionally, the ability to heat an object or area at a distance without any effect on the intervening substance has a large number of applications. For example, systems which require a cycle or a given order of operations may use remote and targeted induction heating. A lighted sign, for example, may have portions that light up at certain times and/or in a certain order. Targeted electromagnetic radiation may be used to activate ferrous switches in the sign, thereby causing the appropriate portion to light up at the appropriate time.

Similarly, an otherwise non-metallic motor may utilize ferrous components to generate heat and/or a spark at appropriate times during the motor's cycle. The control of such targeted induction systems may be computerized such that a user may precisely program the timing and location of electromagnetic radiation to achieve the desired result. As an example, a teacher or salesperson may use induction heat to selectively light a whiteboard, sign, display, etc. to help make a point or highlight a given area.

Additionally, experiments and processes that need intermittent heat, but that require isolation from the ambient environment may also utilize induction to provide the heat. For example, contents of an experiment requiring isolation may be housed in a plurality of sealed, non-ferrous containers. A ferrous element may be inserted into or attached to one or more of the non-ferrous containers that requires intermittent heat to complete the experiment. The ferrous element(s) may be selectively heated at appropriate times to deliver heat without unsealing or otherwise disturbing the contents of the experiment. Crystal growth and cell growth are examples of experiments/procedures that may utilize heat at a distance to facilitate the growth. Heat may also be applied to a substance (such as a PVC pipe) such that the substance is more inclined to emit chemicals. For example, such heating may be used in conjunction with spectroscopy to improve the emissions of a substance so that the emissions are more readily detectable.

Induction heat may also be used to assist with surgical procedures that utilize heat. For example, heat operations featuring ablations may utilize heat that is physically transferred from outside to within the target area. In such a procedure, a small ferrous target may be placed with great precision prior to surgery and may be monitored during the surgery. In the context of atrial fibrillation, the inserted ferrous target may be monitored over many heart cycles, and may be used to transfer heat to a target area to perform an ablation without distress to the patient. The ferrous target may easily be removed once the heat need for the operation is delivered.

Remote and targeted heating may also be used to protect objects and systems that are not readily accessible. For example, ferrous elements may be selectively placed near or around plastic pipes that carry water, and may be used to prevent the pipes from freezing during cold weather conditions. Such pipes may be underground or within walls, and may be otherwise very difficult to access directly. In one embodiment, a computerized system may control the heating of such pipes, and may be configured to automatically activate induction heating of the pipes when the temperature drops below a certain threshold, such as the freezing point.

As discussed herein, clothing may also take advantage of induction heating through the incorporation of ferrous threads that are interwoven into non-ferrous materials. When proximate to an electromagnetic radiation source, the clothing may be heated, providing warmth to the wearer. Such electromagnetic radiation sources may be used in public areas such as bus stops and other areas where individuals are exposed to the elements. Electromagnetic radiation sources for use in heating clothing may also be placed indoors and/or on public transportation such as buses, trains, planes, etc.

Induction heating may also be used to protect trees and plants from unusually cold temperatures. For example, ferrous elements may be placed proximate to the roots of a tree or other plant, and may thereby be used to maintain the roots at a given temperature so that the plant does not die. Such a process may be very beneficial in a tree nursery in which a cold snap likely causes significant losses. In one embodiment, the pots of potted plants, such as flower pots, may include or be made from ferrous material such that the pot may be heated, thereby heating the soil within the pot and the roots of any plants in the pot. For example, a flower pot can be constructed with ferrous metal inserted into the walls of the container or surrounding the walls of the container. A radiation source can be programmed to automatically turn on when a low temperature threshold is reached such that the plants can be safely warmed with no safety concerns and no wires which may become excessively hot. Specifically, radiation travels to the element in or surrounding the flower pot, and heats the pot, which in turn warms the plants. This concept can be extended to large containers for plants, to greenhouses, and to tree roots. Animal cages can similarly be heated. Induction heating may also be used to warm a bee hive without disturbing the bees.

Remote induction heating may also be used by rescue workers to help warm individuals that are trapped or otherwise inaccessible. For example, workers trapped in a mine may have or be provided with ferrous material to receive heat. Targeted electromagnetic radiation may then be used to heat the ferrous material. Similarly, individuals trapped under snow and ice may receive heat via electromagnetic radiation if they are equipped with ferrous material.

The concept of delivering heat into a living body has a number of uses. For example, drug delivery may be facilitated via induction. A drug may be at least partly encased by a small amount of ferrous metal, and may be released by a burst of electromagnetic radiation that is configured to melt the small amount of metal. A drug may similarly be encased by plastic in a pod which is ingested or implanted and which also contains a small amount of ferrous material. When the pod reaches a target area, some electromagnetic radiation heats the ferrous material which melts the plastic and enables the drug to escape and treat the disease or infection. The drug may be delivered into a tumor, for example. No other sources of thermal energy currently in use has such a little of a disturbing impact on the intervening tissue. Targeted induction heating may also be used to enhance vascular permeability, and may even be used to transcend the blood-brain barrier as medical technology improves.

Heat may also be used to change the physical properties of objects such as electrical resistance, length, hardness, etc. The embodiments described herein enable a new level of control in devices made of plastics and other non-ferrous materials. Such devices may include a ferrous element at a key location to serve as an active control. For example, consider two wooden surfaces which are intended to be joined or kept together in certain circumstances and kept apart in other circumstances. One of the wooden surfaces may include a ferrous pin or rod attached thereto, and the other wooden surface may include a plastic receptacle into which the pin or rod fits in a cool (i.e., unheated) condition. Upon heating, the rod or pin increases in diameter such that the rod or pin does not fit into the plastic receptacle. When the heat is removed, the diameter of the rod or pin decreases, thereby allowing it to fit into the plastic receptacle.

Figure 22:
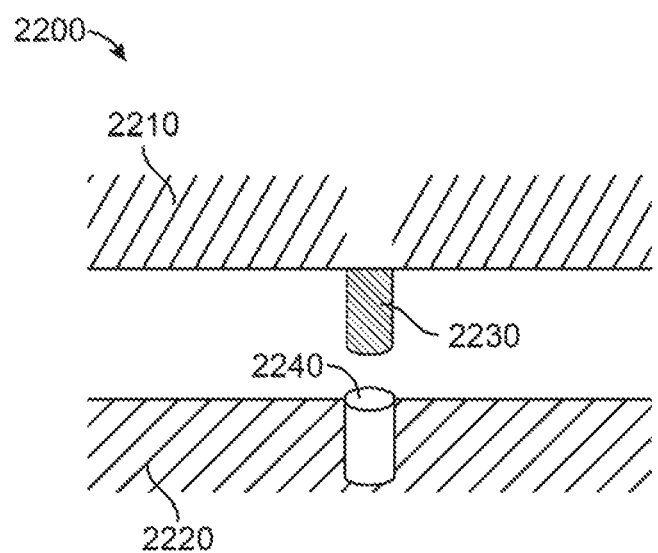
FIG. 22 depicts an attachment mechanism with a male to female connection that is controlled via induction induced heating, in accordance with at least some embodiments of the present disclosure.

Thus, FIG. 22 depicts a device attachment mechanism of a device 2200 having a male to female connection that is controlled via temperature, in accordance with at least some embodiments of the present disclosure. In FIG. 22, the device 2200 includes an upper wood surface 2210 and a lower wood surface 2220. A ferrous rod 2230 placed horizontally across the opening is configured to fit into a plastic receptacle 2240 when the ferrous rod is cool, and the ferrous rod is configured to not fit into the plastic receptacle when the ferrous rod is heated.

In some instances, it is desirable or necessary for two chemicals to be combined at a specific time and/or location which are not accessible or convenient. In an embodiment, the chemicals are placed in adjacent containers or in adjacent parts of the same container, and are separated by an interface which can be melted by the addition of heat. At this interface, a ferrous element of appropriate size is placed and an electromagnetic radiation source is placed nearby. At the appropriate time, the radiation source is turned on, causing the ferrous element to heat up and melt the interface such that the chemicals are combined.

All applications needing heat can be designed to receive such heat using the combination of a radiation source and a ferrous element or material. For example, a thermocouple can be heated in this way, with induction at one end to create a current or control a switch in a circuit. Similarly, a stirling engine can use such induction heating as a source of heat in certain applications where other sources of heat are neither convenient nor safe. The ability to target and control the location and intensity of heating also makes the embodiments described herein useful in situations where it is desirable to dry liquids. This would include wet paint on small (or even large) areas, chemical reactions, biological specimens, liquid surface protectant that has been applied to a surface, and/or any other areas where a warm environment at a specific location will induce a more rapid drying.

Turning now to FIG. 23, an example of a medical device 2300 is shown, in accordance with at least some embodiments of the present disclosure. The medical device 2300 may be configured for implantation within a subject for controlled medicine delivery using induction. The shape, size, and other configuration of the medical device 2300 may vary from one embodiment to another. For example, although the medical device 2300 has been shown as being rectangular in shape, in other embodiments, the shape and size of the medical device may vary based upon the location of implantation of the medical device within the subject, the amount of medicine enclosed within the medical device, the manner of implantation, etc. The medical device 2300 may be constructed of a biocompatible material that is suitable for placement in the subject. For example, if the medical device 2300 is implanted within a human subject, the medical device may be constructed from a material that is suitable for human consumption. In some embodiments, the medical device 2300 may be constructed of a non-ferrous material, although in some cases, it may be desirable to construct the medical device of a ferrous material. In some embodiments, the medical device 2300 may be constructed partially of a ferrous material and partially of a non-ferrous material.

Furthermore, in some embodiments and as shown, the medical device 2300 includes a plurality of compartments 2305. The plurality of compartments 2305 may be integrally or removably formed within the medical device 2300. Each of the plurality of compartments 2305 are configured to hold one or more medicines 2310 that are intended to be released based upon a controlled release function. In some embodiments, each of the plurality of compartments 2305 may be configured to release all of the one or more medicines 2310 stored in that compartment at one time, while in other embodiments, each of the plurality of compartments may be configured to release only a portion of the one or more medicines at one time. Thus, each of the plurality of compartments 2305 may be a single or multi delivery compartment.

The size of each of the plurality of compartments 2305 and the total number of the plurality of compartments within the medical device 2300 may vary from one embodiment to another. In some embodiments, each of the plurality of compartments 2305 may be sized to accommodate the one or more medicines 2310 that are stored within that compartment. Thus, although each of the plurality of compartments 2305 has been shown as being of the same size and shape in FIG. 23, in other embodiments, the size and shape of each of the plurality of compartments within the medical device 2300 may vary based upon the number and amount of the one or more medicines 2310 to be dispensed by a particular one of the plurality of compartments. Additionally, although the plurality of compartments 2305 have been shown as being arranged in a grid pattern, in other embodiments, the arrangement of each of the plurality of compartments within the medical device 2300 may vary. For example, in some embodiments, the plurality of compartments 2305 may be arranged in the order in which they are configured to dispense the one or more medicines 2310 stored therein. For example, those ones of the plurality of compartments 2305 that are configured to dispense the one or more medicines 2310 earlier than other ones of the plurality of compartments may be arranged on or close to a periphery of the medical device 2300, while the remaining ones of the plurality of compartments may be located towards a center of the medical device.

Moreover, each of the plurality of compartments 2305 may be configured as an enclosed structure to contain the one or more medicines 2310 safely before dispensing. The manner in which each of the plurality of compartments 2305 dispenses the one or more medicines 2310 stored therein may vary. In some embodiments, each of the plurality of compartments 2305 may at least partially be coated or constructed with a ferrous material (e.g., nanoparticles), such that by receiving electromagnetic radiation from an electromagnetic radiation source 2315, the ferrous material may be heated. Heat from the ferrous material may be transferred to melt, disintegrate, or otherwise open the plurality of compartments 2305 to release the one or more medicines 2310 stored therein. The amount (e.g., intensity or duration) of electromagnetic radiation needed to heat the ferrous material and open one or more of the plurality of compartments 2305 may vary from other ones of the plurality of compartments. Thus, by knowing the amount of electromagnetic radiation needed to open a given one or more of the plurality of compartments 2305, the one or more medicines 2310 may be selectively dispensed. The amount of electromagnetic radiation needed may be known to a user (e.g., the subject or entity administering/monitoring/controlling the medical device 2300). In other embodiments, mechanisms other than electromagnetic radiation may be used to open each of the plurality of compartments 2305 to dispense the one or more medicines 2310 stored therein. In yet other embodiments, one or more of the plurality of compartments 2305 may not be enclosed. In such embodiments, other mechanisms may be used to store the one or more medicines 2310 within the plurality of compartments 2305 safely before dispensing.

Furthermore, in some embodiments, instead of or in addition to having at least a portion of one or more of the plurality of compartments 2305 constructed from a ferrous material, the one or medicines 2310 may themselves include ferrous substances. For example, in some embodiments, the one or more medicines 2310 may be encased in a housing, which in turn may be enclosed within a ferrous capsule (e.g., constructed out of dietary iron or ferrous nanoparticles, etc.). By heating the ferrous capsule using electromagnetic radiation from the electromagnetic radiation source 2315, the housing surrounding the one or more medicines 2310 may be melted to release the one or more medicines enclosed therein. In other embodiments, the ferrous substance may be provided as a coating on the housing of the one or more medicines 2310, as a coating on a surface of the one or more medicines, mixed within the one or more medicines, or in any other form that may be suitable for releasing the one or more medicines. The number of nanoparticles or other ferrous material used within the ferrous substance may be varied to vary the amount of heat that causes the one or more medicines 2310 to be released. The housing of the one or more medicines 2310 may be composed of a biocompatible material, including an edible polymer, resin, plastic, etc.

Although the medical device 2300 has been described as having the plurality of compartments 2305, in some embodiments, the plurality of compartments may instead be smaller medicine devices arranged and grouped together within the medical device and configured to operate similar to the plurality of compartments described above. Each of the smaller medicine devices may be configured to store the one or more medicines 2310. In yet other embodiments, the one or more medicines 2310 may be bundled together in a packet and multiple such packets may be arranged within the medical device 2300 for dispensing based upon the controlled release function. Thus, various configurations of providing the one or more medicines 2310 within the medical device 2300 are contemplated and considered within the scope of the present disclosure.

Referring still to FIG. 23, the medical device 2300 may be implanted within the subject in a variety of ways. For example, in some embodiments, the medical device 2300 may be small enough for the subject to swallow. In other embodiments, the medical device 2300 may be surgically implanted or may be injected into the bloodstream of the subject. In some embodiments, the medical device 2300 may be magnetically guided to the desired location within the subject's body. Other suitable mechanisms of implantation may be used in other embodiments. Once implanted within the subject, the medical device 2300 may be controlled externally (e.g., from outside the subject) to facilitate release of the one or more medicines 2310 stored within the medical device.

For example, targeted electromagnetic radiation from the electromagnetic radiation source 2315 may be delivered to the medical device 2300. The electromagnetic radiation from the electromagnetic radiation source 2315 may be used to heat the ferrous material provided in one or more of the plurality of compartments 2305 and/or the one or more medicines 2310. Heat from the ferrous material then causes the one or more of the plurality of compartments 2305 to open and/or the housing surrounding the one or more medicines 2310 to melt and release the enclosed medicine.

When no housing is used with the one or more medicines 2310, the heat from the ferrous material may cause the one or more medicines to change form (e.g., melt) and be released. The electromagnetic radiation source 2315 is similar to the electromagnetic radiation sources described above in the present disclosure. The placement of the electromagnetic radiation source 2315 relative to the medical device 2300 may vary. Likewise, multiple instances of the electromagnetic radiation source 2315 may be used to control the heat delivered to the medical device 2300.

In operation, the medical device 2300 may be used to deliver the one or more medicines 2310 based upon the controlled release function. The controlled release function may be include dispensing the one or more medicines 2310 periodically at set time intervals, upon detection of a particular health condition, as needed (e.g., for pain management), or a combination thereof. For example, the medical device 2300 may be an insulin release device that may be configured to release a controlled amount of insulin at specific time intervals or when additional delivery of insulin is needed. Likewise, the medical device 2300 may be a cancer treatment device that may be configured to selectively dispense cancer treatment drugs. In some embodiments, the medical device 2300 may be configured to store medicines to treat/control multiple conditions. In other embodiments, multiple instances of the medical devices 2300, with each instance of the medical device configured to treat/control one or more health conditions may be used.

When dispensing of the one or more medicines 2310 is desired, electromagnetic radiation via the electromagnetic radiation source 2315 may be directed towards the medical device 2310. The amount of electromagnetic radiation (e.g., varying the intensity and/or duration of the electromagnetic radiation) delivered by the electromagnetic radiation source 2315 may be controlled such that ferrous material provided within specific one or more of the plurality of compartments 2305 and/or the one or more medicines 2310 are heated to cause the release of the one or more medicines. Thus, by controlling the amount of electromagnetic radiation that is delivered to the medical device 2300, selective dispensing of the one or more medicines 2310 from the medical device may be achieved.

Therefore, the medical device 2300 may be used for repeated medicine distribution for a period of time or for a specific number of uses. By controlling the electromagnetic radiation that is delivered to the medical device 2300, the distribution of the one or more medicines 2310 from the medical device 2300 may be controlled. The different amounts of electromagnetic radiation that cause the release of specific ones of the one or more medicines 2310 may be stored within a controller 2320. The controller 2320 may control the electromagnetic radiation source 2315 to vary the electromagnetic radiation delivered by the electromagnetic radiation source. Although the controller 2320 is shown separate from the electromagnetic radiation source 2315, in other embodiments, the controller and the electromagnetic radiation source may be integrated together.

In an embodiment, the person in whom the medical device 2300 is placed may wear a small patch with ferrous elements, so that if he or she inadvertently comes into proximity to a source of electromagnetic radiation, the person will feed a small amount of heat from the patch. This heat will alert the person to move out of range of the electromagnetic radiation source so that the ingested drug will not be prematurely released. Alternatively or in addition to the other embodiments, the person may place a ferrous-containing patch over a site of the medical device 2300. The patch would absorb stray electromagnetic radiation and prevent premature release of medication from the medical device 2300.

Although the present disclosure has been described in terms of placing a drug or medicine within the medical device 2300, in other embodiments, other desired substances may be used as well within the medical device. For example, in some embodiments, collagen, bacteria, yeast, sea weed, etc., may be placed within one or more of the plurality of compartments 2305 of the medical device 2300. In other embodiments, other medicinal or non-medicinal substances may be placed within one or more of the plurality of compartments 2305. Furthermore, in some embodiments, different substances may be placed within different ones of the plurality of compartments 2305. For example, in some embodiments, a first substance may be placed in a first compartment and a second substance that is different from the first substance may be placed in a second compartment of the plurality of compartments 2305. The plurality of compartments 2305 may be configured such that the first and second substances do not mix until a barrier separating the compartments in which the first and the second substances are stored is broken.

By virtue of providing the ability to selectively mix two substances within the medical device 2300, the present disclosure provides a mechanism to facilitate a selective chemical reaction within the subject's body. For example, in some embodiments, the medical device 2300 may be positioned within the subject's body. The medical device 2300 may include the plurality of compartments 2305, with at least a subset of neighboring compartments being separated by barriers and carrying one or more substances that are desired to be selectively mixed. When the mixing or the chemical reaction is desired, the electromagnetic radiation source 2315 may be used to heat the ferrous materials within the barrier and transfer the heat from the ferrous material to disintegrate the barriers, thereby separating the compartments holding the substances desired to be mixed. By disintegrating the barriers, multiple smaller compartments are merged into a bigger compartment and the substances within those smaller compartments are led to mix within the bigger compartment to obtain a mixed substance. Additionally, the bigger compartment may also be disintegrated to release the mixed substance into the subject's body, as discussed above by providing electromagnetic radiation from the electromagnetic radiation source 2315.

The barriers that are used to separate the smaller compartments of the plurality of compartments 2305 may be constructed out of, or include, a ferromagnetic material. Further, the amount of heat needed to heat the ferrous material in the barriers may be different from the amount of heat needed to heat the ferrous material in the outside housing of the plurality of compartments 2305. In some embodiments, the barriers may be made of biocompatible plastic having ferrous components. In other embodiments, other biocompatible materials having ferrous components may be used.

In some embodiments, more than a single instance of the medical device 2300 may be placed within the subject's body. Each one of the medical device 2300 may include one or more substances (medicinal and/or non-medicinal) and be configured to be positioned in different locations within the subject's body.

Additionally, in some embodiments, the medical device 2300 or another ferromagnetic material (e.g., ferrous nanoparticles or drugs encased in ferrous substances, etc.) described above, may be used to capture images from within the subject's body. Specifically, the ferrous material may be guided, implanted, or otherwise positioned within the body tissue of the subject that is desired to be photographed. Once in position, electromagnetic radiation may be delivered to heat the ferrous material. The heat generated by the ferrous material may be transferred to the surrounding tissue, which absorbs the heat and thermoelastically expands or generates thermoelastic noise to create ultrasonic waves. The ultrasonic waves may be detected using ultra sonic transducers. Thus, the ferrous materials may also be used for medical imaging purposes.

Turning now to FIG. 24, a pipe 2400 is shown, in accordance with some embodiments of the present disclosure. The pipe 2400 may be constructed out of polyvinyl chloride (PVC) or any other material that is commonly used. Pipes exposed to lower or below freezing temperatures are often prone to freezing over and bursting. To prevent these pipes from bursting, in some embodiments, a ferromagnetic sleeve 2405 may be provided around the pipe 2400. The ferromagnetic sleeve 2405 may be composed of, or may include, ferrous materials that are configured to be heated by electromagnetic radiation from electromagnetic radiation source 2410. The heat from the ferromagnetic sleeve 2405 is transferred to the pipe 2400, thereby heating the body of the pipe and preventing the fluid inside the pipe from freezing and bursting the pipe. In some embodiments, the electromagnetic radiation source 2410 may be configured to turn on automatically by the lower temperatures surrounding the pipe 2400. In other embodiments, the electromagnetic radiation source 2410 may be connected to a controller, which in turn may control the electromagnetic radiation source to deliver the electromagnetic radiation to the ferromagnetic sleeve 2405.

Further, although the pipe 2400 is shown as completely encompassed by the ferromagnetic sleeve 2405 in FIG. 24, in other embodiments, only a portion of the pipe may be encompassed. Further, protecting the pipe 2400 from bursting is simply one example. In other embodiments, the ferromagnetic sleeve 2405 may be used around a tree or plant to protect the tree or plant from damage in colder temperatures. In other embodiments, the ferromagnetic sleeve 2405 may be used around other objects that are at risk of damage from colder temperatures. The ferromagnetic sleeve 2405 may be constructed to be flexible to at least somewhat mold around the object that the ferromagnetic sleeve is designed to protect. In some embodiments, the ferromagnetic sleeve 2405 may be in contact with the pipe 2400 or the object that the ferromagnetic sleeve is protecting. In other embodiments, the ferromagnetic sleeve 2405 may be placed at a small distance from the pipe 2400 or the other object.

In some embodiments, control of the heating elements described herein may be implemented at least in part as computer-readable instructions stored on a computer-readable medium, such as a computer memory or storage device. Upon execution of the computer-readable instructions by a processor, the computer-readable instructions may cause the computing device to perform the operations by directing the radiation source to begin in a desired fashion.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

What is claimed is:

1. A method comprising:

positioning a medical device within a subject, wherein the medical device comprises a plurality of compartments including a first compartment and a second compartment separated by a barrier comprising a first amount of ferrous material, wherein the first compartment is configured to hold a first substance and the second compartment is configured to hold a second substance, and wherein the first compartment and the second compartment comprise a second amount of ferrous material;

delivering a first amount of electromagnetic radiation, by an electromagnetic radiation source, to the medical device for heating the first amount of the ferrous material for disintegrating the barrier and causing the first substance and the second substance to form a combined substance; and delivering a second amount of the electromagnetic radiation, by the electromagnetic radiation source, for heating the second amount of ferrous material for disintegrating the first compartment and the second compartment for releasing the combined substance.

2. The method of claim 1, wherein positioning the medical device within the subject comprises one of surgically implanting the medical device within the subject and injecting the medical device in a bloodstream of the subject.

3. The method of claim 1, wherein the medical device is configured to be swallowed by the subject.

4. The method of claim 1, wherein each of the plurality of compartments is coated with the second amount of ferrous material, and wherein heating the second amount of ferrous material opens at least one of the plurality of compartments.

5. The method of claim 1, wherein the plurality of compartments comprises a third compartment holding a third substance, and wherein the third substance is encased within a housing and the housing is covered with a ferrous capsule, and wherein heating the ferrous capsule melts the housing for releasing the third substance from the housing.

6. The method of claim 1, wherein values of the first amount of electromagnetic radiation and the second amount of electromagnetic radiation are stored within a controller.

7. The method of claim 6, wherein a time interval is associated with each of the plurality of compartments, wherein the time interval is stored within the controller and determines when each of the plurality of compartments is to be disintegrated, and wherein the controller heats the plurality of compartments based on the time interval.

8. The method of claim 1, further comprising placing a ferrous patch on the subject, wherein heat from the ferrous patch alerts the subject of inadvertent proximity to stray electromagnetic radiation.

9. A system, comprising:

a medical device configured to be positioned within a subject, wherein the medical device comprises a plurality of compartments including a first compartment and a second compartment;

wherein the first compartment and the second compartment are separated by a barrier comprising a first amount of ferrous material;

wherein the first compartment is configured to hold a first substance and the second compartment is configured to hold a second substance;

wherein the first compartment and the second compartment comprise a second amount of ferrous material;

wherein the barrier is configured to be disintegrated upon heating the first amount of ferrous material with a first amount of electromagnetic radiation to allow the first substance and the second substance to form a combined substance; and wherein the first compartment and the second compartment are configured to be disintegrated for releasing the combined substance upon heating the second amount of ferrous material with a second amount of electromagnetic radiation.

10. The system of claim 9, further comprising an electromagnetic radiation source configured to deliver the first amount of electromagnetic radiation for heating the first amount of ferrous material for disintegrating the barrier and the second amount of electromagnetic radiation for heating the second amount of ferrous material for disintegrating the first compartment and the second compartment.

11. The system of claim 10, further comprising a controller configured to:

determine the first amount of electromagnetic radiation and the second amount of electromagnetic radiation needed to heat the first amount of ferrous material and the second amount of ferrous material, respectively; and vary electromagnetic radiation delivered from the electromagnetic radiation source based upon the first amount of electromagnetic radiation and the second amount of electromagnetic radiation.

12. The system of claim 9, wherein the medical device comprises a non-ferrous material.

13. The system of claim 9, further comprising a ferrous patch configured to be positioned on the subject and alert the subject of inadvertent proximity to stray electromagnetic radiation.

14. The system of claim 9, wherein the plurality of compartments that are to be disintegrated earlier in time are positioned adjacent to a periphery of the medical device relative to the plurality of compartments that are to be disintegrated later in time.

15. The system of claim 9, wherein the medical device is associated with a control release function stored within a controller associated with the medical device, wherein the control release function determines the first amount of electromagnetic radiation and the second amount of electromagnetic radiation needed to heat the first amount of ferrous material and the second amount of ferrous material, respectively.

16. The system of claim 9, wherein the first substance is different from the second substance.

17. The system of claim 9, wherein the combined substance is obtained by a chemical reaction between the first substance and the second substance.

18. The system of claim 9, wherein the barrier is formed from a biocompatible plastic comprising the first amount of ferrous material.

* * * * *